US009233913B2

United States Patent
Kong et al.

(10) Patent No.: US 9,233,913 B2
(45) Date of Patent: Jan. 12, 2016

(54) AMINO ACID DERIVATIVES FOR THE TREATMENT OF NEUROPATHIC PAIN

(71) Applicant: Xianqi Kong, Dollard-des-Ormeaux (CA)

(72) Inventors: Xianqi Kong, Dollard-des-Ormeaux (CA); Nigel Levens, Beaconsfiled (CA); Serge Lamothe, Boisbriand (CA); Mohammed Atfani, Laval (CA); Stephane Ciblat, Montreal (CA); Lucie Jette, Montreal (CA)

(73) Assignee: Xianqi Kong, Dollard-des-Ormeaux, QC (CA)

( * ) Notice: Subject to any disclaimer, the term of this patent is extended or adjusted under 35 U.S.C. 154(b) by 0 days.

(21) Appl. No.: 14/020,284

(22) Filed: Sep. 6, 2013

(65) Prior Publication Data

US 2014/0171507 A1  Jun. 19, 2014

Related U.S. Application Data

(63) Continuation of application No. 13/289,897, filed on Nov. 4, 2011, now abandoned, which is a continuation-in-part of application No. PCT/CA2010/000670, filed on Apr. 30, 2010.

(60) Provisional application No. 61/215,490, filed on May 6, 2009.

(51) Int. Cl.
| | |
|---|---|
| *C07C 69/75* | (2006.01) |
| *C07C 229/28* | (2006.01) |
| *C07C 229/32* | (2006.01) |
| *C07C 229/36* | (2006.01) |
| *C07D 207/09* | (2006.01) |
| *C07D 307/16* | (2006.01) |
| *C07D 307/54* | (2006.01) |
| *C07D 307/81* | (2006.01) |
| *C07D 307/83* | (2006.01) |
| *C07D 333/24* | (2006.01) |

(52) U.S. Cl.
CPC .............. *C07C 229/28* (2013.01); *C07C 229/32* (2013.01); *C07C 229/36* (2013.01); *C07D 207/09* (2013.01); *C07D 307/16* (2013.01); *C07D 307/54* (2013.01); *C07D 307/81* (2013.01); *C07D 307/83* (2013.01); *C07D 333/24* (2013.01); *C07C 2101/08* (2013.01); *C07C 2101/14* (2013.01); *C07C 2101/16* (2013.01); *C07C 2101/18* (2013.01)

(58) Field of Classification Search
CPC ........................................................ C07C 69/75
USPC .......................................................... 560/126
See application file for complete search history.

(56) References Cited

FOREIGN PATENT DOCUMENTS

| WO | 2008116107 A2 | 9/2008 |
| WO | 2008141446 A1 | 11/2008 |

OTHER PUBLICATIONS

Rose, 2002, Anaesthesia, vol. 57, p. 451-46.*
Diabetic neuropathy, Jun. 3, 2015, http://www.mayoclinic.org/diseases-conditions/diabetic-neuropathy/basics/definition/con-20033336?p=1.*
Field, Mark J. et al., "Channel α2-δ Ligands for the Treatment of Neuropathic Pain", J. Med. Chem., 2007, vol. 50, pp. 2569-2575.
Supplementary European Search Report with regard to EP10771932 dated Nov. 19, 2012.

* cited by examiner

*Primary Examiner* — Michael Barker
*Assistant Examiner* — Karen Cheng
(74) *Attorney, Agent, or Firm* — BCF LLP

(57) ABSTRACT

The invention relates to compounds, to compositions comprising the same and uses thereof for the prevention or treatment of pain, e.g neuropathic pain while having neutral or beneficial effect on metabolic parameters.

19 Claims, 4 Drawing Sheets

A)

* Significantly different from control values

B)

* Significantly different from control values

A)

B)

A)

B)

F, 97%, t$_{1/2}$ 6.8 hr

AMINO ACID DERIVATIVES FOR THE TREATMENT OF NEUROPATHIC PAIN

RELATED APPLICATIONS

This is a continuation of U.S. application Ser. No. 13/289,897 filed Nov. 4, 2011, which is a continuation-in-part of PCT international application number PCT/CA2010/000670 filed Apr. 30, 2010, which claims priority to U.S. provisional application No. 61/215,490 filed on May 6, 2009.

FIELD OF THE INVENTION

The invention relates to compounds, to compositions comprising the same and uses thereof for the prevention or treatment of pain, e.g neuropathic pain.

BACKGROUND OF THE INVENTION

Neuropathic pain (or neuralgia) is generally defined as non-nociceptive pain, in fact, neuropathic pain is produced by a change in neurological function or structure as opposed to activation of pain receptor cells in the case of nociceptive pain.

Diabetic neuropathy is a common complication of type II diabetes that can affect virtually every tissue of the body and induce significant morbidity and mortality. Pain affecting the feet and ankles which is often severe, is the most common symptom of the condition. Duration of diabetes and poor glycemic control appears to be responsible to some extent for nerve damage that ultimately is perceived as painful impulses.

Treatment of diabetic neuropathy is challenging and is currently far from optimal. In fact, neuropathic pain is recognized as one of the most difficult pain syndromes to treat. Currently available therapeutics are modestly to moderately effective in relieving symptoms and are limited by side effects and drug-drug interactions. At the present time, only two drugs are officially approved for the symptomatic treatment of diabetic neuropathy: pregabalin (structurally related to gabapentin) and duloxetine. Both have troublesome side effects, including somnolence and dizziness. More particularly, pregabalin, and also gabapentin, are associated with body weight gain which can worsen the metabolic control in patients with type II diabetes.

There is a need for a therapeutic having better or similar analgesic properties as the currently available treatment but with less adverse effects, and more particularly with beneficial or neutral metabolic effect.

SUMMARY OF THE INVENTION

The invention relates to α-amino acid analogs, to compositions comprising the same and their therapeutic uses. According to one aspect, the compound of the invention is a compound selected from the compounds of any one of Formulae I to VI, including any specific embodiments thereof, a compound selected from Compounds 1 to 30, or a compound of any one of sections a) to e) herein defined, or a pharmaceutically acceptable salt, solvate, prodrug, or ester thereof. In another aspect, the invention relates to a compound of any one of Formulae I to VI, wherein the configuration of the carbon α to the carboxyl is the same as the L-configuration of natural amino acids. Aspects of the invention provide compounds of Formulae II or IV. Another aspect of the invention provides compounds of Formulae II or IV, wherein the configuration of the carbon α to the carboxyl is the same as the L-configuration of natural amino acids. Aspects of the invention provide compounds of Formula II. Another aspect of the invention provides compounds of Formula II, wherein the configuration of the carbon α to the carboxyl is the same as the L-configuration of natural amino acids. The invention also further relates to a compound selected from the group consisting of Compounds 3-5, 11, 13, 15, 17, 19, 23, 24, 26, 27, 29 and the compounds of section d). The invention also further relates to a compound selected from the group consisting of Compounds 6-8, 10, 12, 14, 16, 18, 21, 22, 25, 28, 30, and the compounds of any one of sections a), b), c) or e) herein described. The invention also further relates to a compound selected from the group consisting of Compounds 6 to 8, or Compounds 7 and 8. The invention also further relates to Compound 7. The invention also further relates to Compound 8.

According to another aspect, the invention pertains to pharmaceutical compositions comprising at least one compound of the invention as herein described.

According to other aspects, the invention relates to the use of a compound as herein defined for the treatment of neuropathic pain. The invention also further relates to the use of a compound as herein defined for the treatment of diabetic neuropathy. The invention also further relates to the use of a compound as herein defined for the treatment of diabetic neuropathy while being neutral of beneficial to metabolic symptoms, such as glucose/insulin levels and body weight. The invention also further relates to the use of a compound as herein defined for the treatment of diabetic neuropathy while improving glucose control and/or without body weight gain or reduced body weight. The invention also relates to the use of a compound of the invention in the manufacture of a medicament for the treatment of any of the diseases and conditions herein described.

Another aspect of the invention also relates to methods of treating neuropathic pain in a subject in need thereof comprising the step of administering a therapeutically effective amount of a compound of the invention. The invention also relates to methods of treating diabetic neuropathy in a subject in need thereof comprising the step of administering a therapeutically effective amount of a compound of the invention. The invention also relates to methods of treating diabetic neuropathy while having a neutral or beneficial effect on metabolic symptoms, such as glucose/insulin levels and body weight of a subject in need of such treatment, the method comprising the step of administering a therapeutically effective amount of a compound of the invention. The invention also relates to methods of treating diabetic neuropathy, improving glucose control and/or reducing body weight of a subject in need of such treatment, the method comprising the step of administering a therapeutically effective amount of a compound of the invention.

Other aspects of the invention include the use of the compounds of the invention in the treatment of diseases and conditions treatable by drugs with affinity to an $\alpha_2\delta$ subunit of voltage-gated N-type calcium ion channels. Examples of such diseases and conditions include, without limitation, neuropathy, neuropathic pain, diabetic neuropathy, post-herpetic neuralgia, epilepsy, and fibromyalgia.

In yet another aspect, the invention includes the use of the compounds of the invention in the control of pain, and more particularly nerve pain. Other aspects of the invention include the use of the compounds of the invention in the treatment of a disease or condition selected from neuropathy, neuropathic pain, diabetic neuropathy, post-herpetic neuralgia, fibromyalgia, migraine headaches, post-operative chronic pain, nerve pain associated with spinal cord injury, multiple sclerosis, and nystagmus.

Additional objects, advantages and features of the present invention will become more apparent upon reading of the following non-restrictive description of preferred embodiments which are exemplary and should not be interpreted as limiting the scope of the invention.

DETAILED DESCRIPTION OF THE INVENTION

I. Definitions

Figure 1:
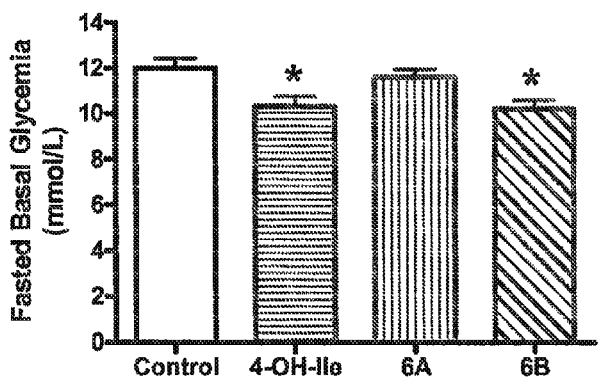
FIG. 1A shows fasted basal glycemia in DIO-mice treated with Compounds 6A and 6B, (2S,3R,4S)-4-hydroxyisoleucine (4-OH-Ile), and vehicle.
FIG. 1B shows fasted basal insulinemia in DIO-mice treated with Compounds 6A and 6B, (2S,3R,4S)-4-hydroxyisoleucine (4-OH-Ile) and vehicle.
Figure 1:
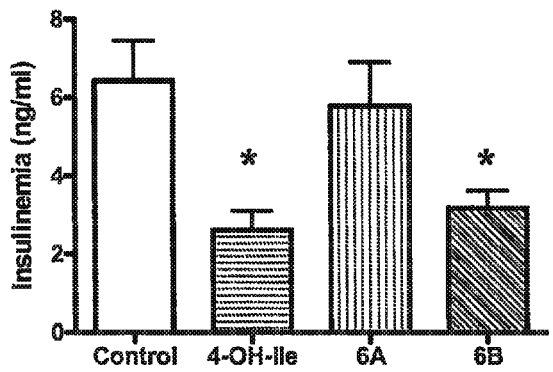

All technical and scientific terms used herein have the same meaning as commonly understood by one ordinary skilled in the art to which the invention pertains. For convenience, the meaning of certain terms and phrases used herein are provided below.

To the extent the definitions of terms in the publications, patents, and patent applications incorporated herein by reference are contrary to the definitions set forth in this specification, the definitions in this specification control. The section headings used herein are for organizational purposes only, and are not to be construed as limiting the subject matter disclosed.

It should be noted that, the singular forms "a", "an", and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The chemical structures herein are drawn according to the conventional standards known in the art. Thus, where an atom, such as a carbon atom, as drawn appears to have an unsatisfied valency, then that valency is assumed to be satisfied by a hydrogen atom even though that hydrogen atom is not necessarily explicitly drawn. Hydrogen atoms should be inferred to be part of the compound.

The symbol "—" in general represents a bond between two atoms in the chain. Thus $CH_3$—O—$CH_2$—CH($R_1$)—$CH_3$ represents a 2-substituted-1-methoxypropane compound. In addition, the symbol "—" also represents the point of attachment of the substituent to a compound. Thus for example aryl($C_1$-$C_6$)alkyl- indicates an arylalkyl group, such as benzyl, attached to the compound through the alkyl moiety.

Where multiple substituents are indicated as being attached to a structure, it is to be understood that the substituent can be the same or different. Thus for example "$R_m$ optionally substituted with 1, 2 or 3 $R_q$ groups" indicates that $R_m$ is substituted with 1, 2, or 3 $R_q$ groups where the $R_q$ groups can be the same or different.

As used herein, the term "Compounds of the present invention" and equivalent expressions refer to compounds mentioned herein as being useful for at least one purpose of the invention, e.g., those encompassed by structural Formulae such as Formulae I to VI and their different aspects and embodiments, and includes specific compounds disclosed herein such as encompassed by those Formulae and to specifically mentioned compounds such as those disclosed in Table 1 or the following sections a) to e), as well as their pharmaceutically acceptable salts and solvates. Embodiments herein may exclude one or more of the compounds of the invention. Compounds may be identified either by their chemical structure and/or chemical name. When the chemical structure and chemical name conflict, the chemical structure is determinative of the identity of the compound. The chemical structures disclosed herein encompass all possible enantiomers and stereoisomers of the illustrated compounds including the stereoisomerically pure form (e.g., geometrically pure, enantiomerically pure, or diastereomerically pure) and enantiomeric and stereoisomeric mixtures if applicable. Enantiomeric and stereoisomeric mixtures can be resolved into their component enantiomers or stereoisomers using separation techniques or chiral synthesis techniques well known to the skilled artisan, e.g., chiral chromatography (such as chiral HPLC), immunoassay techniques, or the use of covalently (such as Mosher's esters) and non-covalently (such as chiral salts) bound chiral reagents to respectively form a diastereomeric mixture which can be separated by conventional methods, such as chromatography, distillation, crystallization or sublimation, the chiral salt or ester is then exchanged or cleaved by conventional means, to recover the desired isomers. The compounds may also exist in several tautomeric forms including the enol form, the keto form, and mixtures thereof. Accordingly, the chemical structures depicted herein encompass all possible tautomeric forms of the illustrated compounds. The disclosed compounds also include isotopically labeled compounds where one or more atoms have an atomic mass different from the atomic mass most abundantly found in nature, for example, without limitation, $^2H(D)$, $^3H(T)$, $^{11}C$, $^{13}C$, $^{14}C$, $^{15}N$, $^{18}O$, $^{17}O$, etc. Compounds may exist in unsolvated forms as well as solvated forms, including hydrated forms, in general, compounds may be hydrated or solvated. Certain compounds may exist in multiple crystalline or amorphous forms. In general, all physical forms are equivalent for the uses contemplated herein and are intended to be within the scope of the present invention. Further, when partial structures of the compounds are illustrated, brackets or equivalents indicate the point of attachment of the partial structure to the rest of the molecule.

The invention pertains to both salt forms and acid/base forms of the compounds of the invention. For example, the invention pertains not only to the particular salt forms of compounds shown herein as salts, but also the invention includes other pharmaceutically acceptable salts, and the acid and/or base form of the compound. The invention also pertains to salt forms of compounds shown herein.

The term "prodrug" and equivalent expressions refer to agents which can be converted in vitro or vivo directly or indirectly to an active form (see, e.g., R. B. Silverman, 1992, "The Organic Chemistry of Drug Design and Drug Action," Academic Press, Chap. 8; Bundgaard, Hans; Editor. Neth.

(1985), "Design of Prodrugs". 360 pp. Elsevier, Amsterdam; Stella, V.; Bernhardt, R.; Hageman, M.; Oliyai, R.; Maag, H.; Tilley, J. (Eds.) (2007), "Prodrugs: Challenges and Rewards, XVIII, 1470 p. Springer). Prodrugs can be used to alter the biodistribution (e.g., to allow agents which would not typically enter the reactive site of the protease) or the pharmacokinetics for a particular agent. A wide variety of groups have been used to modify compounds to form prodrugs, for example, esters, ethers, phosphates, etc. When the prodrug is administered to a subject, the group is cleaved, enzymatically or non-enzymatically, reductively, oxidatively, or hydrolytically, or otherwise to reveal the active form. As used herein, "prodrug" includes pharmaceutically acceptable salts thereof, or pharmaceutically acceptable solvates as well as crystalline forms of any of the foregoing. Prodrugs can be pharmaceutically active or inactive; and the latter will exert the pharmaceutical activity when it is converted to the parent drug(s).

The term "aliphatic group" includes organic moieties characterized by straight or branched-chains, typically having between 1 and 16 carbon atoms, or having between 1 to 12, 1 to 8, 1 to 5 or 1 to 3 carbon atoms. Aliphatic groups include acyclic alkyl groups, alkenyl groups, and alkynyl groups.

As used herein, the term "acyclic" refers to an organic moiety without ring system.

As used herein, the term "alkyl" refers to saturated hydrocarbons having from one to sixteen carbon atoms, including linear or branched alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, and the like. The term "$C_1$-$C_n$alkyl" refers to an alkyl group having from 1 to the indicated "n" number of carbon atoms.

As used herein, the term "alkenyl" refers to unsaturated hydrocarbons having from two to sixteen carbon atoms, including linear or branched alkenyl groups, and comprising between one and six carbon-carbon double bonds. Examples of alkenyl groups include, without limitation, vinyl, allyl, 1-propen-2-yl, 1-buten-3-yl, 1-buten-4-yl, 2-buten-4-yl, 1-penten-5-yl, 1,3-pentadien-5-yl, and the like. The term alkenyl includes both unsubstituted alkenyl groups and substituted alkenyl groups. The term "$C_2$-$C_n$alkenyl" refers to an alkenyl group having from 2 to the indicated "n" number of carbon atoms.

As used herein, the term "alkynyl" refers to unsaturated hydrocarbons having from two to twelve carbon atoms, including linear or branched alkynyl groups, and comprising between one to six carbon-carbon triple bond. Examples of alkynyl groups include, without limitation, ethynyl, 1-propyn-3-yl, 1-butyn-4-yl, 2-butyn-4-yl, 1-pentyn-5-yl, 1,3-pentadiyn-5-yl, and the like. The term alkynyl includes both unsubstituted alkynyl groups and substituted alkynyl groups. The term "$C_2$-$C_n$alkynyl" refers to an alkynyl group having from 2 to the indicated "n" number of carbon atoms.

Unless the number of carbons is otherwise specified, "lower" as in "lower aliphatic," "lower alkyl," "lower alkenyl," and "lower alkylnyl", as used herein means that the moiety has at least one (two for alkenyl and alkynyl) and equal or less than 6 carbon atoms.

The terms "cycloalkyl", "alicyclic", "carbocyclic" and equivalent expressions refer to a group comprising a saturated or partially unsaturated (non aromatic) carbocyclic ring in a monocyclic or polycyclic ring system, including spiro (sharing one atom) or fused (sharing at least one bond) carbocyclic ring systems, having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl" refers to a cycloalkyl group having from 3 to the indicated "n" number of carbon atoms in the ring structure. Unless the number of carbons is otherwise specified, "lower cycloalkyl" groups as herein used, have at least 3 and equal or less than 8 carbon atoms in their ring structure.

The term "heterocycloalkyl" and equivalent expressions refer to a group comprising a saturated or partially unsaturated (non aromatic) carbocyclic ring in a monocyclic or polycyclic ring system, including spiro (sharing one atom) or fused (sharing at least one bond) carbocyclic ring systems, having from three to fifteen ring members, where one or more (up to six) ring members are substituted or unsubstituted heteroatoms (e.g. N, O, S, P) or groups containing such heteroatoms (e.g. NH, $NR_x$ ($R_x$ is alkyl, acyl, aryl, heteroaryl or cycloalkyl), $PO_2$, SO, $SO_2$, and the like). Heterocycloalkyl groups may be C-attached or heteroatom-attached (e.g. via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, quinolizinyl, and sugars, and the like. The term heterocycloalkyl includes both unsubstituted heterocycloalkyl groups and substituted heterocycloalkyl groups. The term "$C_3$-$C_n$heterocycloalkyl" refers to a heterocycloalkyl group having from 3 to the indicated "n" number of atoms (carbon or heteroatom or group) in the ring structure, including at least one hetero group or atom as defined above. Unless the number of carbons is otherwise specified, "lower heterocycloalkyl" groups as herein used, have at least 3 and equal or less than 8 ring members in their ring structure.

The terms "aryl" and "aryl ring" refer to aromatic groups having 4n+2π(pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The term "$C_6$-$C_n$aryl" refers to an aryl group having from 6 to the indicated "n" number of carbons in the ring structure.

The terms "heteroaryl" and "heteroaryl ring" refer to aromatic groups having 4n+2π (pi) electrons, wherein n is an integer from 1 to 3, in a conjugated monocyclic or polycyclic system (fused or not) and having five to fourteen ring members, including one to six substituted or unsubstituted heteroatoms (e.g. N, O, S) or groups containing such heteroatoms (e.g. NH, $NR_x$ ($R_x$ is alkyl, acyl, aryl, heteroaryl or cycloalkyl), SO, and the like). A polycyclic ring system includes at least one heteroaromatic ring. Heteroaryls may be directly attached, or connected via a $C_1$-$C_3$alkyl group (also referred to as heteroarylalkyl or heteroaralkyl). Heteroaryl groups may be C-attached or heteroatom-attached (e.g. via a nitrogen atom), where such is possible. Examples of heteroaryl groups include, without limitation, pyridyl, imidazolyl, pyrimidinyl, pyrazolyl, triazolyl, tetrazolyl, furyl, thienyl; isooxazolyl, thiazolyl, oxazolyl, isothiazolyl, pyrrollyl, quinolinyl, isoquinolinyl, indolyl, 3H-indolyl, indolinyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofurnayl, and the like. The term heteroaryl includes both unsubstituted heteroaryl groups and substituted heteroaryl groups. The term "$C_5$-$C_n$heteroaryl refers to an heteroaryl group having from 5 to the indicated "n" number of atoms (carbon or heteroatom or group) in the ring structure, including at least one hetero group or atom as defined above.

The terms "heterocycle" or "heterocyclic" or "heterocyclyl" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "amine" or "amino," as used herein, refers to an unsubstituted or substituted moiety of the formula —NR$^a$R$^b$, in which R$^a$ and R$^b$ are each independently hydrogen, alkyl, aryl, or heterocyclyl, or R$^a$ and R$^b$, taken together with the nitrogen atom to which they are attached, form a heterocyclic ring. The term "amide" or "aminocarbonyl" includes compounds or moieties which contain a nitrogen atom which is bound to the carbon of a carbonyl or a thiocarbonyl group. The term acylamino refers to an amino group directly attached to an acyl group as defined herein.

The term "nitro" means —NO$_2$; the terms "halo" and "halogen" refer to bromine, chlorine, fluorine or iodine substituents; the term "thiol", "thio", or "mercapto" means SH; and the term "hydroxyl" or "hydroxy" means —OH. The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The term "alkoxy" or "lower alkoxy" as used herein means an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups and the like. The term alkoxy includes both unsubstituted or substituted alkoxy groups, etc., as well as halogenated alkyloxy groups.

The term "carbonyl" or "carboxy" includes compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group ($C_1$-$C_n$alkyl, $C_1$-$C_n$alkenyl, $C_1$-$C_n$alkynyl, wherein n is an integer from 2 to 10; e.g. acetyl, a cycloalkyl group (e.g. $C_3$-$C_8$cycloalkyl), a heterocyclic group (e.g. $C_3$-$C_8$heterocycloalkyl and $C_5$-$C_6$heteroaryl), an aromatic group (e.g. $C_6$aryl, e.g., benzoyl), and the like. Acyl groups may be unsubstituted or substituted acyl groups (e.g. salicyloyl).

The term "amino acid" generally refers to an organic compound comprising both a carboxylic acid group and an amine group. The term "amino acid" includes both "natural" and "unnatural" or "non-natural" amino acids. Additionally, the term amino acid includes O-alkylated or N-alkylated amino acids, as well as amino acids having nitrogen or oxygen-containing side chains (such as Lys, Orn, or Ser) in which the nitrogen or oxygen atom has been acylated or alkylated. Amino acids may be pure L or D isomers or mixtures of L and D isomers, including racemic mixtures. Amino acid may be α-, or β-, or γ-, or δ-, or ω-amino acid.

The term "natural amino acid" and equivalent expressions refer to amine acids commonly found in naturally occurring proteins. Examples of natural amino acids include, without limitation, alanine (Ala), cystein (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asp), proline (Pro), glutamine (Gln), arginine (Arg), serine (Ser), threonine (Thr), valine (Val), tryptophan (Trp), tyrosine (Tyr), β-alanine (β-ALA), and γ-aminobutyric acid (GABA).

The term "unnatural amino acid" refers loosely to any compound which bears at least one amino group and at least one carboxylic group in the same molecule; and the compound is not a natural product or has not been found in nature at the time being but rather a synthetic chemical entity. Examples of unnatural amino acids include derivatives of natural amino acids including D forms, and α- and β-amino acid derivatives. The terms "unnatural amino acid" and "non-natural amino acid" are used interchangeably herein and are meant to include the same moieties. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): 2-aminoadipic acid (Aad), 3-aminoadipic acid (β-Aad), 2-aminobutyric acid (2-Abu), α,β-dehydro-2-aminobutyric acid (8-AU), 1-aminocyclopropane-1-carboxylic acid (ACPC), aminoisobutyric acid (Aib), 3-aminoisobutyric acid (β-Aib), 2-amino-thiazoline-4-carboxylic acid, 5-aminovaleric acid (5-Ava), 6-aminohexanoic acid (6-Ahx), 2-aminoheptanoic acid (Ahe), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-NH$_2$-Phe), 2-aminopimelic acid (Apm), biphenylalanine (Bip), para-bromophenylalanine (4-Br-Phe), ortho-chlorophenylalanine (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), desmosine (Des), 2,2-diaminopimelic acid (Dpm), 2,3-diaminopropionic acid (Dpr), 2,4-diaminobutyric acid (Dbu), 3,4-dichlorophenylalanine (3,4-Cl$_2$-Phe), 3,4-diflurorphenylalanine (3,4-F$_2$-Phe), 3,5-diiodotyrosine (3,5-I$_2$-Tyr), N-ethylglycine (EtGly), N-ethylasparagine (EtAsn), ortho-fluorophenylalanine (2-F-Phe), meta-fluorophenylalanine (3-F-Phe), para-fluorophenylalanine (4-F-Phe), mete-fluorotyrosine (3-F-Tyr), homoserine (Hse), homophenylalanine (Hfe), homotyrosine (Htyr), hydroxylysine (Hyl), allo-hydroxylysine (aHyl), 5-hydroxytryptophan (5-OH-Trp), 3- or 4-hydroxyproline (3- or 4-Hyp), para-iodophenylalanine (4-I-Phe), 3-iodotyrosine (3-I-Tyr), indoline-2-carboxylic acid (Idc), isodesmosine (Ids), allo-isoleucine (a-Ile), isonipecotic acid (Inp), N-methylisoleucine (MeIle), N-methyllysine (MeLys), mete-methyltyrosine (3-Me-Tyr), N-methylvaline (MeVal), 1-naphthylalanine (1-Nal), 2-naphthylalanine (2-Nal), para-nitrophenylalanine (4-NO$_2$-Phe), 3-nitrotyrosine (3-NO$_2$-Tyr), norleucine (Nle), norvaline (Nva), ornithine (Orn), ortho-phosphotyrosine (H$_2$PO$_3$-Tyr), octahydroindole-2-carboxylic acid (Oic), penicillamine (Pen), pentafluorophenylalanine (F$_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th).

It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more. The term "substituted", when in association with any of the foregoing groups refers to a group substituted at one or more position with substituents such as acyl, amino (including simple amino, mono and dialkylamino, mono and diarylamino, and alkylarylamino), acylamino (including carbamoyl, and ureido), alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, formyl and the like. Any of the above substituents can be further substituted if permissible, e.g. if the group contains an alkyl group, an aryl group, or other.

The term "solvate" refers to a physical association of a compound of this invention with one or more solvent molecules, whether organic or inorganic. This physical association includes hydrogen bonding. In certain instances, the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, hemiethanolates, and the like, preferably hydrates.

A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that takes advantage of an intrinsically basic, acidic or charged functionality on the molecule and that is not biologically or otherwise undesirable. Example of pharmaceutically acceptable salts are also described, for example, in Berge et al., "Pharmaceutical Salts", *J. Pharm. Sci.* 66, 1-19 (1977). Such salts include:

(1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like;

(2) base addition salts, formed when an acidic proton present in the parent compound either is replaced by a metal ion, including, an alkali metal ion (e.g. lithium, sodium, potassium), an alkaline earth ion (e.g. magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like, Pharmaceutically acceptable salts may be synthesized from the parent agent that contains a basic or acidic moiety, by conventional chemical methods. Generally, such salts are prepared by reacting the free acid or base forms of these agents with a stoichiometric amount of the appropriate base or acid in water or in an organic solvent, or in a mixture of the two. Salts may be prepared in situ, during the final isolation or purification of the agent or by separately reacting a purified compound of the invention in its free acid or base form with the desired corresponding base or acid, and isolating the salt thus formed. The term "pharmaceutically acceptable salts" also include zwitterionic compounds containing a cationic group covalently bonded to an anionic group, as they are "internal salts".

All acid, salt, base, and other ionic and non-ionic forms of the compounds described are included as compounds of the invention. For example, if a compound is shown as an acid herein, the salt forms of the compound are also included. Likewise, if a compound is shown as a salt, the acid and/or basic forms are also included.

"Bioavailability" refers to the rate and amount of a drug that reaches the systemic circulation of a patient following administration of the drug or prodrug thereof to the subject and can be determined by evaluating, for example, the plasma or blood concentration-versus-time profile for the drug. Parameters useful in characterizing a plasma or blood concentration-versus-time curve include the area under the curve (AUC), the time to peak concentration ($T_{max}$), and the maximum drug concentration ($C_{max}$). Bioavailability is often expressed as F (%) referring to the ratio in percentage of the AUC of the compound for a specific mode of administration (e.g. orally) over AUC of the compound after an IV administration.

The term "reduction of side effects" of a compound (e.g. a compound of the invention) refers to decreasing the amount of or severity of one or more side effects of the compound by, e.g., 5%, 10%, 20%, 30%, 40%, 50%, 60%, 70%, 80%, 90%, 95%, 99%, or 99.9%, or even 100%, which decrease is with respect to the side effects observed when a patient is treated with gabapentin or pregabalin.

More generally, the terms "lessening" etc., "increasing" etc., refer in context herein to the percentage changes, e.g., by 5%, 10%, 20%, 30%, 40%, 50%, 60%, 70%, 80%, 90%, 95%, 99%, 125%, etc., or even more, e.g., 2, or 4 fold, or even more.

"Pharmaceutically acceptable" refers to drugs, medicaments, inert ingredients etc., which the term describes, suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or state government or listed in the U.S. Pharmacopoeia or other generally recognized pharmacopoeia for use in animals and more particularly in humans.

"Pharmaceutically acceptable vehicle" or "pharmaceutically acceptable carrier" refers to a diluent, adjuvant, excipient, or carrier with which a compound is administered.

"Pharmaceutical composition" refers to at least one compound and at least one pharmaceutically acceptable vehicle or carrier, with which the compound is administered to a patient.

Reference will now be made in detail to certain embodiments of compounds and methods. The disclosed embodiments are not intended to be limiting of the invention.

II. Compounds of the Invention

One aspect of the invention relates to new compounds, α-amino acid derivatives, to compositions comprising the same and uses thereof for the prevention or treatment of pain, e.g. neuropathic pain.

Thus, in one aspect, the invention relates to a compound of Formula I defined as follows:

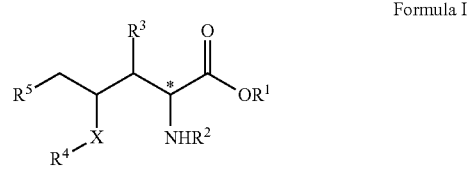

Formula I wherein, $R^1$ is hydrogen, $C_{1-6}$alkyl, $C_{2-6}$alkenyl, $C_{2-6}$alkynyl, $C_{3-6}$cycloalkyl, $C_{3-6}$heterocycloalkyl, $C_6$aryl, or $C_{5-9}$heteroaryl;

$R^2$ is hydrogen, or an N-protecting group;

X is O, NH, or S;

$R^3$ is hydrogen, $C_{1-12}$alkyl, $C_{2-6}$alkenyl, $C_{2-6}$alkynyl, $C_{3-6}$cycloalkyl, $C_{3-6}$heterocycloalkyl, $NH_2$, $NHR^6$, $NR^6R^7$, $OR^6$, halide, or $R^3$ and $R^5$ taken together with their adjacent carbon atoms form a $C_{3-12}$cycloalkyl, $C_{3-12}$heterocycloalkyl, $C_{6-10}$aryl, or $C_{5-10}$heteroaryl; and $R^4$, $R^5$, $R^6$ and $R^7$ are each independently hydrogen, $C_{1-12}$alkyl, or $C_{6-10}$aryl, or $R^4$ and $R^5$ are taken together with their adjacent atoms to form a heterocycloalkyl or heteroaryl group;

wherein when $R^1$, $R^2$, $R^3$, $R^4$, $R^5$, $R^6$ or $R^7$ is a group selected from alkyl, alkenyl, alkynyl, cycloalkyl, heterocycloalkyl, aryl, or heteroaryl, then said alkyl, alkenyl, alkynyl, cycloalkyl, heterocycloalkyl, aryl, or heteroaryl group may be unsubstituted or substituted with a group selected from the group consisting of acyl, unsubstituted amino, alkylamino, dialkylamino, arylamino, diarylamino, alkylarylamino, acylamino, carbamoyl, ureido, alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, and formyl; or a pharmaceutically acceptable salt, prodrug, metabolite, or solvate thereof.

In one embodiment, the compound is a compound of Formula 1 and X is O. In an embodiment, the compound is a compound of Formula I, provided that the compound is not a naturally occurring amino acid. In a subclass of any of the above embodiments, the compound is a compound of Formula I, provided that when $R^1$, $R^2$ and $R^4$ are all hydrogen atoms, $R^3$ is hydrogen or a $C_{1-10}$alkyl, then $R^5$ is not a $C_{1-6}$alkyl. In another embodiment, $R^2$ is a protecting group selected from the group selected from the group consisting of acyl, and amino-substituted acyl, such as an amino acid residue (e.g. valyl, leucyl and isoleucyl). In yet another embodiment, $R^2$ is hydrogen and all other groups are as previously defined.

In another aspect, the invention relates to a compound of Formula II defined as follows:

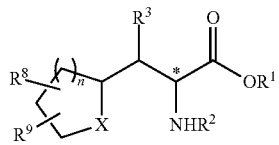

Formula II wherein,
X is O, NH, or S;
$R^3$ is hydrogen, $C_{1-12}$alkyl, $C_{2-6}$alkenyl, $C_{2-6}$alkynyl, $C_{3-6}$cycloalkyl, $C_{3-6}$heterocycloalkyl, $NH_2$, $NHR^6$, $NR^6R^7$, $OR^6$, or halide;
$R^8$ and $R^9$ are each independently hydrogen, $C_{1-12}$alkyl, $C_{6-10}$aryl, $NH_2$, $NHR^6$, $NR^6R^7$, $OR^6$, halide, cycloalkyl, alkylenyl, arylalkyl, or $R^8$ and $R^9$ are taken together with their adjacent atoms to form a spiro or fused heterocycloalkyl or heteroaryl group, or $R^8$ and $R^9$ are attached to the same carbon atom and together with the adjacent carbon atom form a carbonyl;
n is an integer selected from 0 to 3; and
$R^1$, $R^2$, $R^6$, $R^7$ and X are as previously defined;
wherein when $R^1$, $R^2$, $R^3$, $R^4$, $R^5$, $R^6$, $R^7$, $R^8$ or $R^9$ is a group selected from alkyl, alkenyl, alkynyl, cycloalkyl, heterocycloalkyl, aryl, or heteroaryl, then said alkyl, alkenyl, alkynyl, cycloalkyl, heterocycloalkyl, aryl, or heteroaryl group may be unsubstituted or substituted with a group selected from the group consisting of acyl, unsubstituted amino, alkylamino, dialkylamino, arylamino, diarylamino, alkylarylamino, acylamino, carbamoyl, ureido, alkylcarbonyloxy, arylcarbonyloxy, alkoxycarbonyloxy, alkoxycarbonyl, carboxy, carboxylete, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, and formyl;
or a pharmaceutical acceptable salt, prodrug, metabolite, or solvate thereof.

In one embodiment, X is oxygen and all other groups are as previously defined. In another embodiment, X is oxygen, n is 1, $R^3$ is a hydrogen and all other groups are as previously defined. In another embodiment, X is oxygen, n is 1, $R^3$ is a hydrogen, the chiral center C* is in the S configuration and all other groups are as previously defined. In another embodiment, X is O, n is 1, $R^2$ is a protecting group selected from the group selected from the group consisting of acyl, and amino-substituted acyl, such as an amino acid residue (e.g. valyl, leucyl and isoleucyl) and all other groups are as previously defined. In yet another embodiment, X is O, n is 1, $R^2$ is hydrogen and all other groups are as previously defined. In another embodiment, X is oxygen, n is 0, and all other groups are as previously defined. In another embodiment, X is oxygen, n is 2 and all other groups are as previously defined. In another embodiment, X is oxygen, n is 3 and all other groups are as previously defined. In a further embodiment, the compound is a compound of Formula II, wherein X is oxygen, n is 1 and $R^3$ is hydrogen. In another embodiment, the compound is a compound of Formula II, wherein X is oxygen, n is 1 and $R^3$ is $C_{1-6}$alkyl, or a $C_{1-4}$alkyl, or a methyl, ethyl, propyl, or i-propyl group. In yet another embodiment, X is NH and all other groups are as previously defined. In further embodiment, X is sulfur and all other groups are as previously defined.

In another aspect, the invention relates to a compound of Formula III defined as follows:

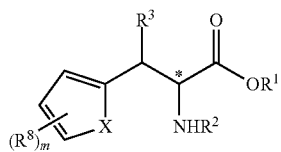

Formula III wherein,
m is an integer from 1 to 3, wherein $R^8$ is the same or different in each instance;
$R^1$, $R^2$, $R^3$, $R^8$ and X are as previously defined;
or a pharmaceutically acceptable salt, prodrug, metabolite, or solvate thereof.

In an embodiment, $R^3$ is a hydrogen, n is 1 or 2 and all other groups are as previously defined. In one embodiment, X is oxygen and all other groups are as previously defined. In yet another embodiment, X is NH and all other groups are as previously defined. In further embodiment, X is sulfur and all other groups are as previously defined.

In yet another aspect, the invention relates to a compound of Formula IV defined as follows:

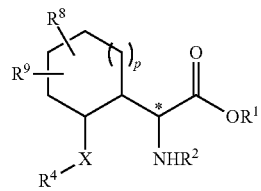

Formula IV wherein,
p is an integer from 1 to 2; and
$R^1$, $R^2$, $R^4$, $R^8$, $R^9$, and X are as previously defined;
or a pharmaceutically acceptable salt, prodrug, metabolite, or solvate thereof.

In one embodiment, X is oxygen and all other groups are as previously defined. In another embodiment, X is oxygen, p is 1 and all other groups are as previously defined. In another embodiment, X is oxygen, p is 2 and all other groups are as previously defined. In another embodiment, X is oxygen, p is 1, $R^4$ is a hydrogen, the chiral center C* is in the S configuration and all other groups are as previously defined. In another embodiment, X is O, p is 1, $R^2$ is a protecting group selected from the group selected from the group consisting of acyl, and amino-substituted acyl, such as an amino acid residue (e.g. valyl, leucyl and isoleucyl) and all other groups are as previously defined. In yet another embodiment, X is O, p is 1, $R^2$ is hydrogen and all other groups are as previously defined. In another embodiment, $R^2$ is a protecting group selected from the group selected from the group consisting of acyl, and amino-substituted acyl, such as an amino acid residue (e.g. valyl, leucyl and isoleucyl). In yet another embodiment, $R^2$ is hydrogen and all other groups are as previously defined. In yet another embodiment, X is NH and all other groups are as previously defined. In a further embodiment, X is sulfur and all other groups are as previously defined.

In yet another aspect, the invention relates to a compound of Formula V defined as follows:

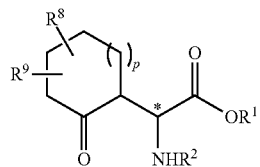

Formula V wherein,

R¹, R², R⁸, R⁹, X and p are as previously defined;

or a pharmaceutically acceptable salt, prodrug, metabolite, or solvate thereof.

In one embodiment, p is 1 and all other groups are as previously defined. In another embodiment, p is 2 and all other groups are as previously defined.

In yet another aspect, the invention relates to a compound of Formula VI defined as follows:

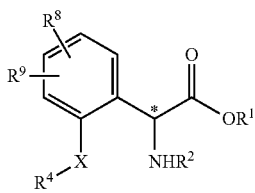

Formula VI wherein,

R¹, R², R⁴, R⁸, R⁹, and X are as previously defined;

or a pharmaceutically acceptable salt, prodrug, metabolite, or solvate thereof.

In one embodiment, the invention relates to a compound of any one of Formulae I to VI, wherein the compound is a mixture of compounds where the chiral center C* is in the S or the R configuration and all other groups are as previously defined, or substantially pure S configuration, or substantially pure R configuration, preferably in the S configuration. In another embodiment, the invention relates to a compound of any one of Formulae I to VI, wherein the compound is a mixture of compounds where the chiral center C* is has the same configuration as D and L amino acid and all other groups are as previously defined, or substantially pure L configuration, or substantially pure D configuration, preferably in the L configuration.

Exemplary compounds include, but are not limited to, the compounds of Table 1:

TABLE 1

| ID | Structure |
|---|---|
| 1 | (structure) |
| 2 | (structure) |
| 3 | (structure) |
| 4 | (structure) |
| 5 | (structure) |
| 6 | (structure) |
| 7 | (structure) |
| 8 | (structure) |
| 9 | (structure) |
| 10 | (structure) |
| 11 | (structure) |

TABLE 1-continued

| ID | Structure |
|----|-----------|
| 12 | (2-hydroxycyclohexyl)glycine stereoisomer |
| 13 | (2-hydroxycyclohexyl)glycine stereoisomer |
| 14 | (2-hydroxycyclohexyl)glycine stereoisomer |
| 15 | (2-hydroxycyclohexyl)glycine stereoisomer |
| 16 | (2-hydroxycyclohexyl)glycine stereoisomer |
| 17 | (2-hydroxycyclohexyl)glycine stereoisomer |
| 18 | (2-hydroxycyclohexyl)glycine stereoisomer |
| 19 | (2-hydroxycyclohexyl)glycine stereoisomer |
| 20 | (2-oxocyclohexyl)glycine |

TABLE 1-continued

| ID | Structure |
|----|-----------|
| 21 | (2-oxocyclohexyl)glycine stereoisomer |
| 22 | (2-oxocyclohexyl)glycine stereoisomer |
| 23 | (2-oxocyclohexyl)glycine stereoisomer |
| 24 | (2-oxocyclohexyl)glycine stereoisomer |
| 25 | (2-hydroxyphenyl)glycine stereoisomer |
| 26 | (2-hydroxyphenyl)glycine stereoisomer |
| 27 | (2-hydroxycyclopentyl)glycine |
| 28 | (2-hydroxycyclopentyl)glycine stereoisomer |
| 29 | (2-hydroxycycloheptyl)glycine stereoisomer |

TABLE 1-continued
| ID | Structure |
|----|-----------|
| 30 | 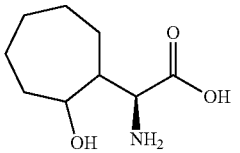 [SMILES: N[C@H](C(=O)O)C1CCCCCC1O] |
or a pharmaceutically acceptable salt, solvate, prodrug or ester thereof.
Other examples of exemplary compounds of the invention are as follows, or a pharmaceutically acceptable salt, solvate, prodrug or ester thereof:
a. Tetrahydrofuran-Based Compounds with L-amino Acid Configuration
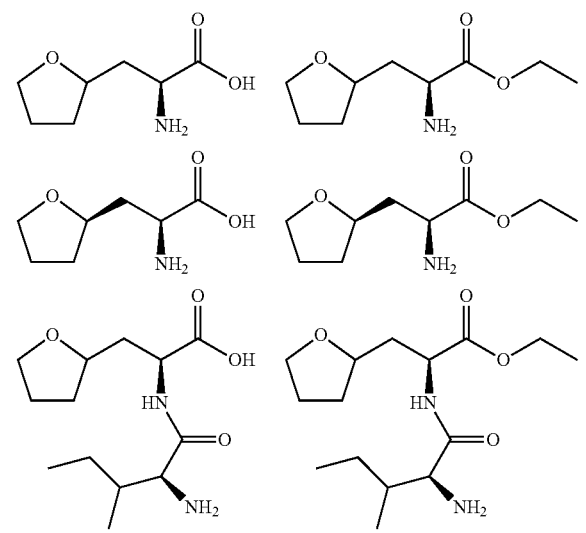
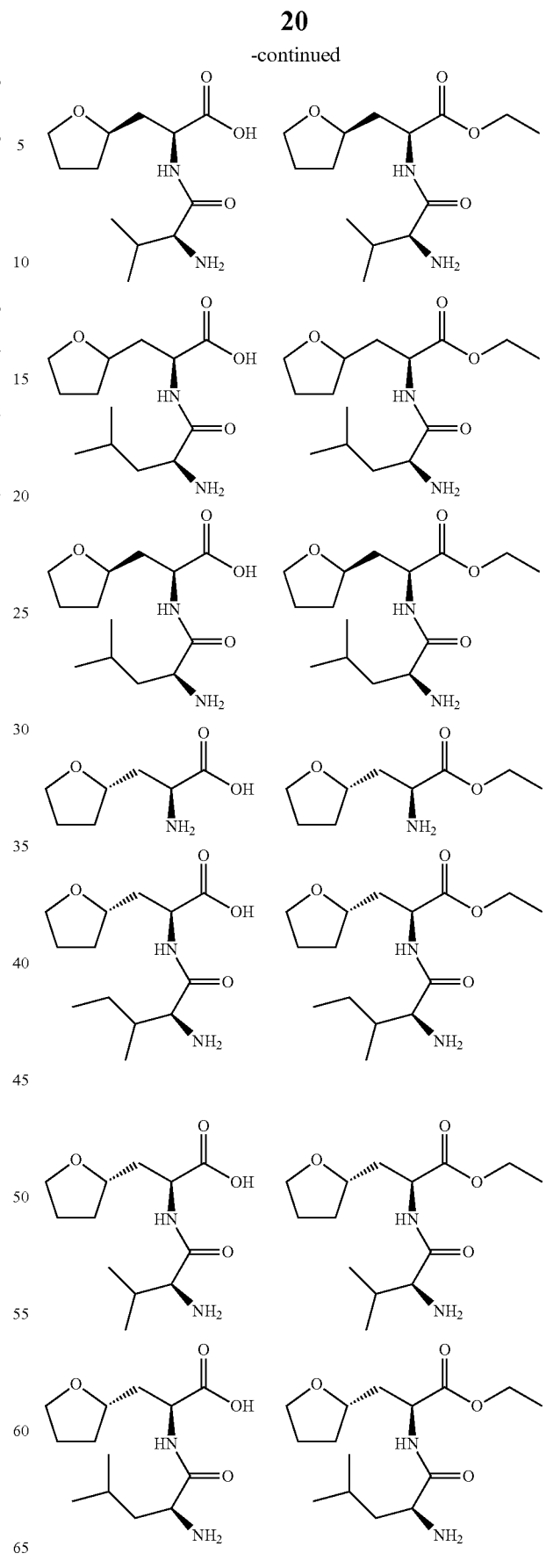

b. Thiophen-Based:
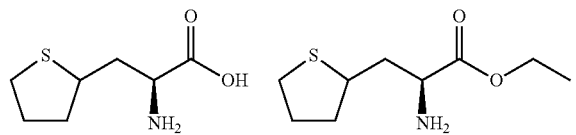
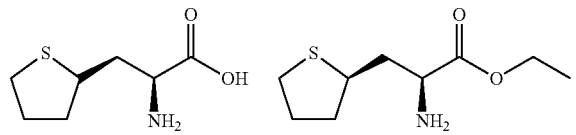
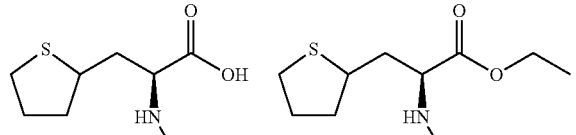
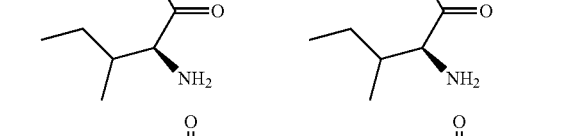
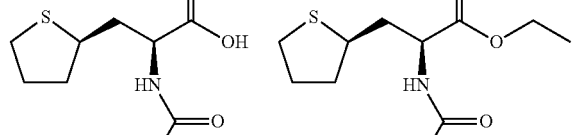
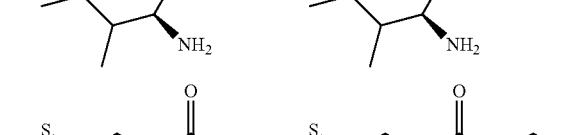
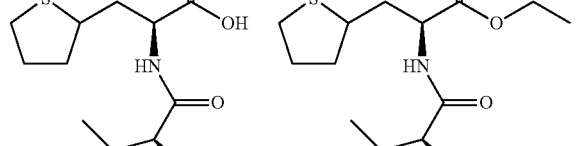
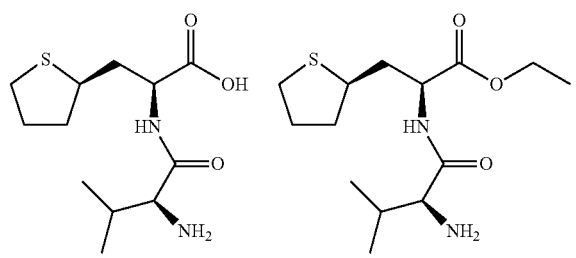
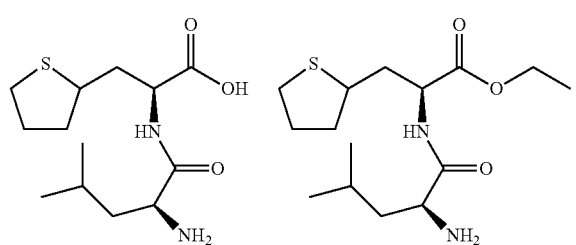
-continued
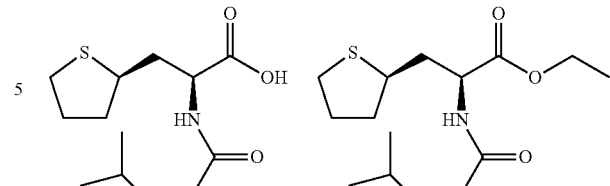
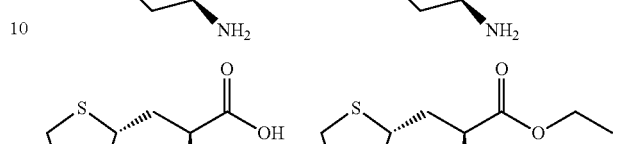
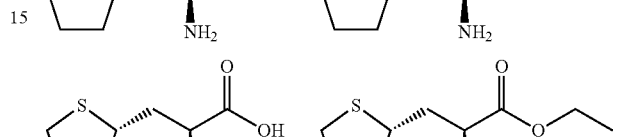
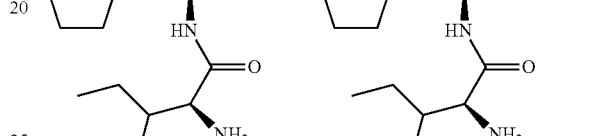
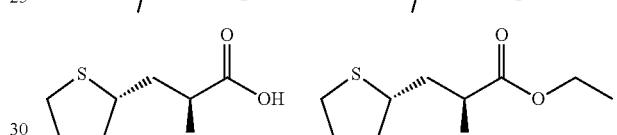
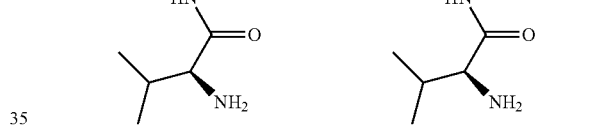
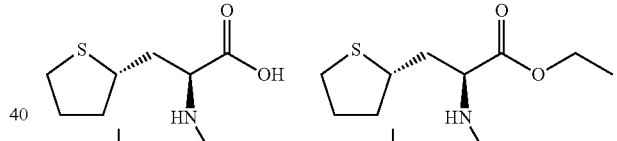
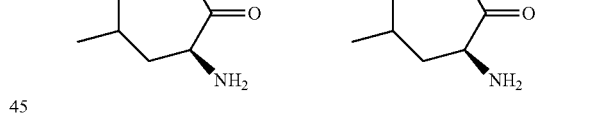
c. Pyrrolidine-Based Examples
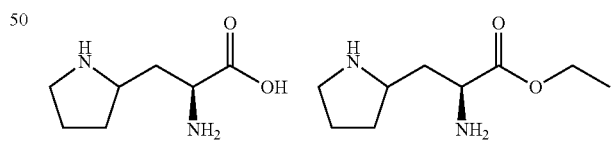
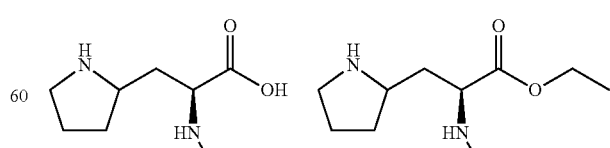
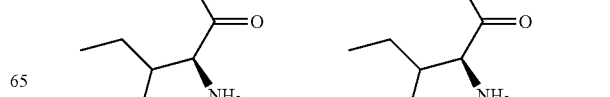

-continued

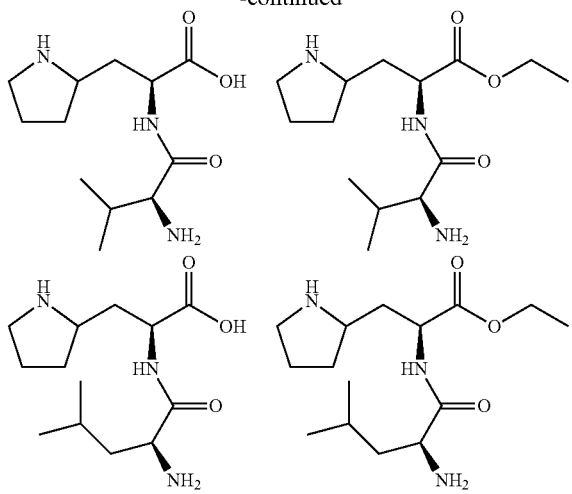

d. Furan and Benzofuran-Based

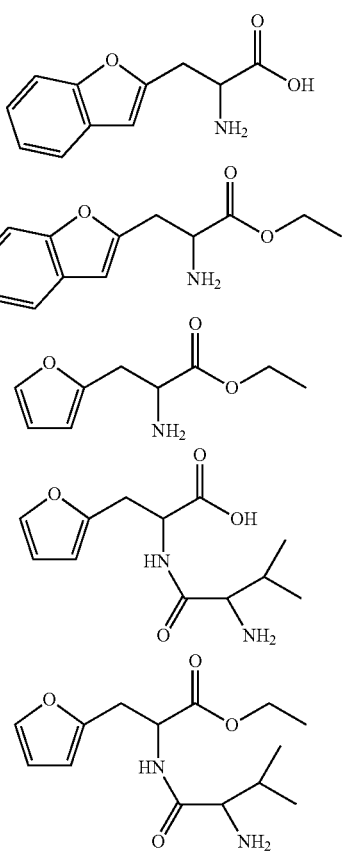

e. Cyclohexane-Based

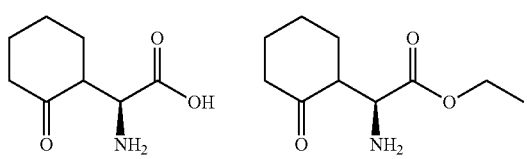

-continued

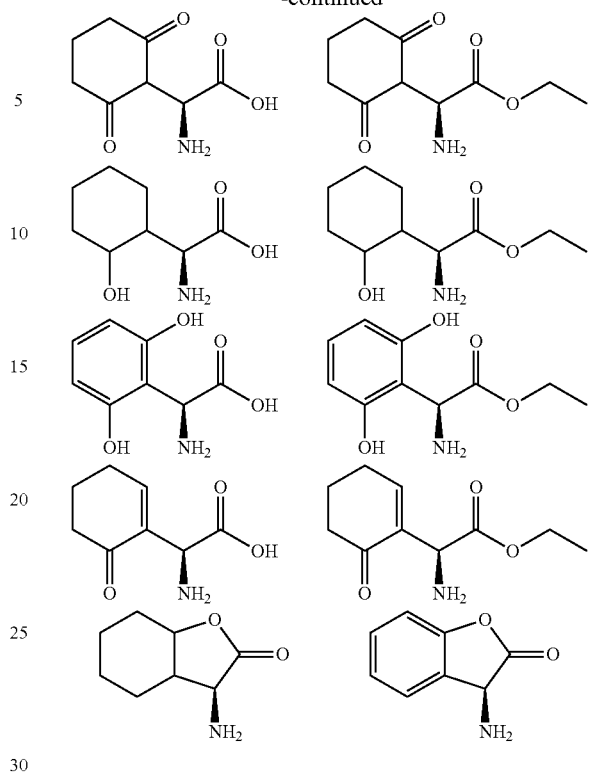

or a pharmaceutically acceptable salt, solvate, prodrug or ester of any one of the above-referenced compound.

Although theory of operation is discussed herein, for specific compound structures, including all generic structural formulas and specific names and formulas of compounds, the invention is not limited by any such theories unless specifically stated otherwise. Thus, all uses of all novel compounds are encompassed by the invention, irrespective of mechanism or theory of operation.

The compounds according to the invention can be further analyzed, tested or validated using a variety of methods, techniques and assays known in the art. There is a substantial amount of published scientific and patent literature concerning the discussed diseases and conditions and the standard assays, techniques and methods for assessing and measuring the safety, biological activity, pharmacokinetics properties and efficacy of the compounds. Therefore, one skilled in the art can readily evaluate and test the compounds according to the invention by using the information in the public domain. Nevertheless, the Exemplification section provides examples of biological assays that can be conducted to assess the instant compounds.

III. Synthesis of the Compounds of the Invention

In general, the compounds of the present invention may be prepared by the methods illustrated in the Examples hereinafter and/or other conventional methods, using readily available and/or conventionally preparable starting materials, reagents and conventional synthesis procedures. In these reactions, it is also possible to make use of variants which are in themselves known, but are not mentioned here. Certain novel and exemplary methods of preparing the inventive compounds are described in the Exemplification section. Such methods are within the scope of this invention. Functional and structural equivalents of the compounds described herein and which have the same general properties, wherein one or more simple variations of substituents are made which do not adversely affect the essential nature or the utility of the compound are also included.

The compounds described herein can be prepared by any number of methods known or obvious to those skilled in the art. The synthetic approaches are chosen depending of the functional groups present or introduced in the starting material used and the compound to be produced.

IV. Pharmaceutical Compositions

Preferably, the compounds of the invention are formulated prior to administration into pharmaceutical compositions using techniques and procedures well known in the art. Accordingly, in another embodiment, the present invention relates to pharmaceutical compositions (e.g. solid or semi-solid mixtures, solutions, suspensions or emulsions) comprising effective amounts of one or more compounds according to any of the Formulae herein and a pharmaceutically acceptable vehicle, as well as methods of using and manufacturing such pharmaceutical compositions.

The pharmaceutical compositions are formulated into suitable administration (orally, parenterally, (IV, IM, depo-IM, SC, and depo-SC), sublingually, intranasal (inhalation), intrathecally, topically, or rectally). Suitable pharmaceutically acceptable vehicles include, without limitation, any non-immunogenic pharmaceutical carrier or diluent suitable for oral, parenteral, nasal, mucosal, transdermal, topical, intrathecal, rectal, intravascular (IV), intraarterial (IA), intramuscular (IM), and subcutaneous (SC) administration routes, such as phosphate buffer saline (PBS). Also, the present invention includes such compounds which have been lyophilized and which may be reconstituted to form pharmaceutically acceptable formulations for administration, as by intravenous, intramuscular, or subcutaneous injection. Administration may also be intradermal or transdermal.

Preferably, the pharmaceutical composition of the invention is suitable for oral administration. The formulations may conveniently be presented in unit dosage form and may be prepared by any methods well known in the art of pharmacy. In general, the formulations are prepared by uniformly and intimately bringing into association a compound of the present invention with a pharmaceutically acceptable vehicle (e.g. an inert diluent or an assimilable edible, liquid or finely divided solid (or both), carrier) and, optionally, one or more accessory ingredients and then, if necessary, shaping the product. The amount of the therapeutic agent in such therapeutically useful compositions is such that a suitable dosage will be obtained.

Formulations of the invention suitable for oral administration may be in the form of capsules (e.g. hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), and the like, each containing a predetermined amount of a compound of the present invention as an active ingredient. A compound of the present invention may also be administered as a bolus, electuary or paste, or incorporated directly into the subject's diet. Moreover, the compounds can be orally formulated to (a) provide for instant or rapid drug release (i.e., have no coating on them); (b) be coated, e.g., to provide for sustained drug release over time; or (c) be enterically coated for better gastrointestinal tolerability or protection from degradation in the stomach.

In solid dosage forms of the invention for oral administration the active ingredient is typically mixed with one or more pharmaceutically acceptable carriers, such as sodium citrate or dicalcium phosphate, or any of the following: fillers or extenders (e.g. starches, lactose, sucrose, glucose, mannitol, or silicic acid); binders (e.g. carboxymethylcellulose, alginates, gelatin, polyvinyl pyrrolidone, sucrose or acacia); humectants (e.g. glycerol); disintegrating agents (e.g. agar-agar, calcium carbonate, potato or tapioca starch, alginic acid, certain silicates, and sodium carbonate); solution retarding agents (e.g., as paraffin); absorption accelerators (e.g. quaternary ammonium compounds); wetting agents (e.g., cetyl alcohol and glycerol monostearate); absorbents (e.g., kaolin and bentonite clay); lubricants (e.g. talc, calcium stearate, magnesium stearate, solid polyethylene glycols, sodium lauryl sulfate, and mixtures thereof); and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Peroral compositions typically also include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants.

Pharmaceutical compositions suitable for injectable use include sterile aqueous solutions (where water soluble) or dispersions, and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof. Solvent or dispersion medium suitable for injectable use are, for example, water, ethanol, polyols (for example, glycerol, propylene glycol, and liquid polyethylene glycol, and the like), suitable mixtures thereof, and vegetable oils. Proper fluidity is maintained, for example, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Pharmaceutical formulations are also provided which are suitable for administration as an aerosol, by inhalation. These formulations comprise a solution or suspension of the desired compound of any Formula herein or a plurality of solid particles of such compound(s). As a liquid, the formulation will comprise, for example, a water-soluble compound of the invention, or a salt thereof, in a carrier which comprises water. A surfactant may be present which lowers the surface tension of the formulation sufficiently to result in the formation of droplets within the desired size range when subjected to nebulization. On the other hand, solid particles can be obtained by processing the solid form of a compound, or a salt thereof, in any appropriate manner known in the art, such as by micronization. The liquid droplets or solid particles should have a particle size in the range of about 0.5 to about 5 microns. The size of the solid particles or droplets will be, for example, from about 1 to about 2 microns. The desired formulation may be placed in a small chamber and nebulized. Nebulization may be accomplished by compressed air or by ultrasonic energy to form a plurality of liquid droplets or solid particles comprising the agents or salts. In this respect, commercial nebulizers are available to achieve this purpose.

The compositions of this invention can also be administered topically to a subject, e.g., by the direct lying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of an agent of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Other compositions useful for attaining systemic delivery of the subject agents include sublingual buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included. The compound(s) of the invention may also be administered parenterally, intraperitoneally, intraspinally, or intracerebrally. For such compositions, the compound(s) of the invention can be prepared in glycerol, liquid polyethylene glycols, and mixtures thereof and in oils. Under ordinary conditions of storage and use, these preparations may contain a preservative to prevent the growth of microorganisms.

To administer the compound(s) of the invention by other than parenteral administration, it may be useful to coat the compounds(s) with, or co-administer the compound(s) with a material to prevent its inactivation. For example, the compound(s) of the invention may be administered to a subject in an appropriate carrier, for example, liposomes, or a diluent. Pharmaceutically acceptable diluents include saline and aqueous buffer solutions. Liposomes include water-in-oil-water CGF emulsions as well as conventional liposomes.

Pharmaceutical compositions according to the invention may also be coated by conventional methods, typically with pH or time-dependent coatings, such that the compound(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Dosage forms provide the pharmaceutical compound upon in vivo administration of a pharmaceutical composition of the invention to a human patient. It is understood that appropriate doses depend upon a number of factors within the knowledge of the ordinarily skilled physician, veterinarian, or researcher (e.g. see Wells et al. eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)). The dose(s) of the compound(s) of the invention will vary, for example, depending upon a variety of factors including, but not limited to: the activity, biological and pharmacokinetic properties and/or side effects of the compound being used; the age, body weight, general health, gender, and diet of the subject; the time of administration, the route of administration, the rate of excretion, and any drug combination, if applicable; the effect which the practitioner desires the compound to have upon the subject; and the properties of the compound being administered (e.g. bioavailability, stability, potency, toxicity, etc). Such appropriate doses may be determined using the assays described herein or known in the art. When one or more of the compounds of the invention is to be administered to humans, a physician may for example, prescribe a relatively low dose at first, subsequently increasing the dose until an appropriate response is obtained.

There are no particular limitations on the dose of each of the compounds for use in the composition of the present invention. Exemplary doses include milligram or microgram amounts of the compound per kilogram of subject or sample weight (e.g., about 50 micrograms per kilogram to about 500 milligrams per kilogram, about 1 milligram per kilogram to about 100 milligrams per kilogram, about 1 milligram per kilogram to about 50 milligram per kilogram, about 1 milligram per kilogram to about 10 milligrams per kilogram, or about 3 milligrams per kilogram to about 5 milligrams per kilogram). Additional exemplary doses include doses of about 5 to about 500 mg, about 25 to about 300 mg, about 25 to about 200 mg, about 50 to about 150 mg, or about 50, about 100, about 150 mg, about 200 mg or about 250 mg, and, preferably, daily or twice daily, or lower or higher amounts.

It is generally advantageous to formulate parenteral compositions in dosage unit form for ease of administration and uniformity of dosage. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical vehicle. The specification for the dosage unit forms of the invention may vary and are dictated by and directly dependent on (a) the unique characteristics of the therapeutic agent and the particular therapeutic effect to be achieved, and (b) the limitations inherent in the art of compounding such a therapeutic agent for the prevention of treatment of neuropathic pain.

Administration of the compounds and compositions of the present invention to a subject to be treated can be carried out using known procedures, at dosages and for periods of time effective to achieved a desired purposes. Dosage regimens can be adjusted to provide the optimum therapeutic response. For example, several divided doses may be administered daily or the dose may be proportionally reduced as indicated by the exigencies of the therapeutic situation. Preferably, the compound(s) of the invention is administered at a therapeutically effective dosage sufficient to reduce neuropathic pain symptoms in a subject, preferably a human subject while being neutral or beneficial to a metabolic disorder, such as diabetes.

The compound(s) of the invention may be packaged as part of a kit, optionally including a container (e.g. packaging, a box, a vial, etc). The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

V. Methods of Use of the Compounds and Compositions of the Invention

Another aspect of the invention pertains to a method for treating neuropathic pain in a subject by administering an effective amount of a compound of the present invention. The term "subject" includes living organisms with neuropathic pain, or which are susceptible to neuropathic pain (or neuralgia), e.g. diabetic neuropathy. Examples of subjects include humans, monkeys, cows, rabbits, sheep, goats, pigs, dogs, cats, rats, mice, and transgenic species thereof. The term "subject" preferably includes animals susceptible to states characterized by metabolic diseases and/or neuropathic pain, e.g. mammals, e.g. primates, e.g. humans. The animal can also be an animal model for a disorder, e.g., a pain mouse model, or an obese or diabetic mouse or rat model.

In certain embodiments of the invention, the human subject is in need of treatment by the methods of the invention, and is selected for treatment based on this need. A subject in need of treatment is art-recognized, and includes subjects that have been identified as having neuropathic pain, has a symptom of such a disease or disorder, or is at risk of such a disease or disorder, and would be expected, based on diagnosis, e.g., medical diagnosis, to benefit from treatment (e.g., curing, healing, preventing, alleviating, relieving, altering, remedying, ameliorating, improving, or affecting the disease or disorder, the symptom of the disease or disorder, or the risk of the disease or disorder).

For example, the human subject may be a human over 30 years old, human over 40 years old, a human over 50 years old, a human over 60 years old, a human over 70 years old, a human over 80 years old. The subject may be a female human, including a postmenopausal female human, who may be on hormone (estrogen) replacement therapy. The subject may also be a male human. In another embodiment, the subject is under 40 years old.

In some embodiments, the subject may have symptoms of a metabolic disease or condition, such as diabetes (e.g. type II diabetes), metabolic syndrome, obesity, etc. In another embodiment, the subject may have symptoms of type II diabetes and be overweight. In one embodiment, the subject has a body mass index (BMI) of 25 or more, a BMI between 25 and 30, or a BMI of 30 or more. The Body Mass Index, or BMI is a measure of a person's weight taking into account their height. It is given by the formula: BMI equals a person's weight (mass) in kilograms divided by the square of the person's height in meters.

"Preventing" or "prevention" is intended to refer at least the reduction of likelihood or the risk of (or susceptibility to) acquiring a disease or disorder (i.e., causing at least one of the clinical symptoms of the disease not to develop in a patient that may be exposed to or predisposed to the disease but does not yet experience or display symptoms of the disease). The term "prevention" or "preventing" is also used to describe the administration of a compound or composition of the invention to a subject who is at risk of (or susceptible to) such a disease or condition. Patients amenable to treatment for prevention of the disease or condition include individuals at risk of the disease or condition but not showing symptoms, as well as patients presently showing symptoms. Predisposing factors identified or proposed in the scientific literature include, among others, environmental factors predisposing a subject to neuropathic pain; past history of infection by viral and bacterial agents predisposing a subject to neuropathic pain (e.g. shingles); and metabolic disorders predisposing a subject to neuropathic pain (e.g. type II diabetes).

"Treating" or "treatment" of any disease or disorder refers, in some embodiments, to ameliorating at least one disease or disorder (i.e., arresting or reducing the development of the disease or at least one of the clinical symptoms thereof). In certain embodiments "treating" or "treatment" refers to ameliorating at least one physical parameter. In certain embodiments, "treating" or "treatment" refers to inhibiting the disease or disorder, either physically, (e.g., stabilization of a discernible symptom), physiologically, (e.g., stabilization of a physical parameter), or both. In certain embodiments, "treating" or "treatment" refers to delaying the onset of the disease or disorder. The term "treating" refers to any indicia of success in the treatment or amelioration of an injury, pathology or condition, including any objective or subjective parameter such as abatement; remission; diminishing of symptoms or making the injury, pathology or condition more tolerable to the subject; improving a subject's physical or mental well-being, reducing or pain experienced by the patient; and, in some situations additionally improving at least one parameter of a metabolic disorder (e.g. glucose tolerance, insulin secretion, reducing weight gain, etc). The treatment or amelioration of symptoms can be based on objective or subjective parameters; including the results of a physical examination or the subject's evaluation of symptoms, or of a test known in the art (e.g. glucose level, etc).

As used herein the term "therapeutically effective amount" refers to the amount or dose of the compound, upon single or multiple dose administration to the patient, which provides the desired effect in the patient under diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the size, age, and general health of the subject; the specific disease(s) involved; the degree of or involvement or the severity of the disease; the response of the individual subject; the particular compound administered; the mode of administration; the bioavailability characteristics of the preparation administered; the dose regimen selected; the use of concomitant medication; and other relevant circumstances.

Improvement in condition is present within the context of the present invention if there is a measurable difference between the performances of subjects treated using the methods of the invention as compared to members of a placebo group, historical control, or between subsequent tests given to the same subject. The invention also pertains to a method for treating, including slowing or stopping neuropathic pain in a disease or condition associated with metabolism, by administering to a subject an effective amount of a therapeutic compound of the invention, wherein the compound is neutral to or improves any metabolic symptom.

It is to be understood that wherever values and ranges are provided herein, e.g., in ages of subject populations, dosages, and blood levels, all values and ranges encompassed by these values and ranges, are meant to be encompassed within the scope of the present invention. Moreover, all values in these values and ranges may also be the upper or lower limits of a range.

In certain embodiments, the compounds and composition according to the invention can be used in combination therapy with at least one other therapeutic or nutraceutic agent. The compounds of the invention when administered in association with at least one other (same or different) therapeutic agent (s), can act additively or, in certain embodiments, synergistically.

The compounds of the invention can be administered prior, subsequent to or concomitantly with the other therapeutic or nutraceutic agent. The compositions of the present invention can be administered with the other therapeutic agent as part of the same pharmaceutical composition as, or in a different composition from, that containing the compounds of the present invention. The at least one other agent can be effective for treating the same or different disease, disorder, or condition. Preferably, the other agent is suitable for the treatment of symptoms of neuropathy, neuropathic pain, or a metabolic disorder, e.g. diabetes, metabolic syndrome, obesity, and the like.

Methods of the present invention include administration of one or more compounds or pharmaceutical compositions of the present invention and one or more other therapeutic agents provided that the combined administration does not inhibit the therapeutic efficacy of the one or more compounds of the present invention and/or does not produce adverse combination effects.

In some aspects, the combination therapy comprises alternating between administering a composition of the present invention and a composition comprising another therapeutic agent, e.g., to minimize adverse side effects associated with a particular drug. When a compound of the present invention is administered concurrently with another therapeutic agent that potentially can produce adverse side effects including, but not limited to, toxicity, the therapeutic agent can advantageously be administered at a dose that falls below the threshold at which the adverse side effect is elicited. A pharmaceutical composition can also further comprise substances to enhance, modulate and/or control release, bioavailability, therapeutic efficacy, therapeutic potency, stability, and the like.

The compounds or pharmaceutical compositions of the present invention include, or can be administered to a patient together with, another therapeutic drug that may be available over-the-counter or by prescription. Therapeutic drugs as well as nutraceuticals useful in a combination with a therapeutic compound of the present invention are known to the skilled artisan. Preferred therapeutic drugs to be used with the compounds or pharmaceutical compositions of the present invention are therapeutic drugs useful in the prevention or treatment of, but not limited to, neuropathic pain, diabetes and other metabolism disorders, or anti-obesity agents.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, issued patents, and published patent applications cited throughout this application are hereby incorporated by reference. The invention is further illustrated by the following examples, which should not be construed as further limiting.

EXAMPLES

The Examples set forth herein below provide exemplary syntheses of certain representative compounds of the invention. Also provided are exemplary methods for assaying the compounds of the invention for in vitro stability, microsomes metabolism and mouse bioavailability.

Unless otherwise indicated, all numbers expressing quantities of ingredients, reaction conditions, concentrations, properties, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

The present invention also relates to novel compounds and the synthesis thereof. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques. In some cases, the compounds may be commercially available.

Example 1

Chemical Synthesis of Selected Compounds

Accordingly, the following examples are presented to illustrate how selected compounds according to the invention may be prepared.

Preparation of Compounds 6, 7 and 8

Method 1: Preparation and Separation of a Mixture of Diastereoisomers

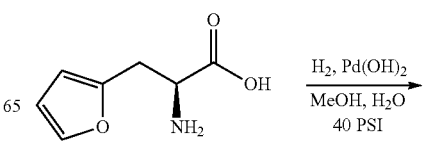

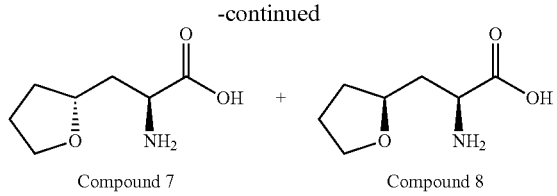

Compound 7          Compound 8

To a degassed (with $N_2$) solution of (2S)-3-(2-furyl)alanine (1.5 g, 10 mmol) in a 10:1 mixture of $H_2O$:MeOH (100 mL) was added palladium hydroxide (Pd(OH)$_2$, 100 mg). The mixture was stirred for 24 h under hydrogen (40 psi). The mixture was filtered through Celite (with methanol) and the filtrate was evaporated under vacuum. A mixture of the two diasteromers was obtained (Compound 6). The two diastereomers were separated by HPLC (Polar column, 2% isocratic acetonitrile in water (0.05% trifluoroacetic acid)) to afford Compound 6A (400 mg) and Compound 6B (530 mg). Compound 6A is of the same chemical structure as Compound 7 while Compound 6B is of the same chemical structure as Compound 8. The structure of each was confirmed by diastereoselective synthesis.

Method 2: Diastereoselective Synthesis of Both Diastereoisomers

This method allows the diastereoselective synthesis of both diastereoisomers and the determination of the stereochemistry of the stereocenters.

Step 1: Preparation of (2S)- and (2R)-2-(iodomethyl)tetrahydrofuran

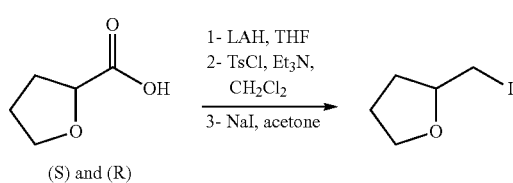 [SMILES: O=C(O)C1CCCO1 ; ICC1CCCO1]

(S) and (R)

1—Method a: A solution of tetrahydrofuran-2-carboxylic acid (5 g, 43 mmol) in THF (30 mL) was added dropwise to a −20° C. solution of LAN (1M in diethylether, 65 mL, 65 mmol). The mixture was gradually warmed up to room temperature and stirred overnight. After being cooled to 0° C., ethyl acetate (20 mL) was added, followed by addition of $H_2O$ (20 mL). The mixture was stirred at room temperature for 1 h, and filtered through Celite (using ethyl acetate). The filtrate was concentrated on a rotary evaporator; and the residual alcohol was used in the next step without further purification.

Method b: A 1 M solution of lithium aluminum hydride in tetrahydrofuran (75 mL, 75 mmol) was cooled to −78° C. Tetrahydrofuran-2-carboxyiic acid (5.4 mL, 50.0 mmol) was slowly added dropwise ($H_2$ released). The solution was stirred at −78° C., slowly warmed over several hours and stirred at room temperature overnight. Water (2.9 mL) was added slowly while the mixture was cooled to 0° C. At room temperature, a 5N aqueous sodium hydroxide solution (2.3 mL) was added to the reaction mixture followed by water (8.7 mL). The mixture was diluted with THF (100 mL), stirred for 4 hour, and filtered on a büchner funnel (rinsed with THF (150 mL)). The resulting solution was concentrated under reduced pressure, co-evaporated with toluene, re-dissolved in dichloromethane and concentrated under reduced pressure, giving the corresponding alcohol (4.9 g, 96%) as a colorless, slightly volatile, oil.

2—The residual alcohol from method (a) was dissolved in a mixture of triethylamine (30 mL, 215 mmol) and dlchloromethane (300 mL). To the solution was added p-toluenesulfonyl chloride (8.2 g, 43 mmol). The mixture was stirred at room temperature for 24 h, and a 1N HCl solution was added to adjust pH until 3. The organic layer was separated and the aqueous layer was extracted with dichloromethane (2×100 mL). The combined organic layers were dried over magnesium sulfate and filtered. The filtrate was evaporated under reduced pressure. The residual material was purified by chromatography on silica gel (Hexane/ethyl acetate, 99/1 to 70/30 linear gradient), providing the corresponding tosylate (5.3 g) as a colorless liquid.

3—To a solution of the tosylate (7.4 g, 28.9 mmol) in acetone (290 mL) was added sodium iodide (43.4 g, 289 mmol) and the reaction was stirred overnight at 70° C. in an oil bath. The reaction mixture was cooled to room temperature, filtered on a büchner funnel, and rinsed with acetone. The filtrate was concentrated under reduced pressure without heating to give a wet orange solid. This residual solid was stirred in diethyl ether (250 mL), filtered through a plug of silica gel, and rinsed with diethyl ether. The filtrate was concentrated to dryness (without heating) and the residual material was submitted to purification by silica gel chromatography (hexanes/diethyl ether, 2:1) to give 2-(iodomethyl)tetrahydrofuran (5.42 g, 89%).

Step 2: Synthesis of Compounds 7 and 8

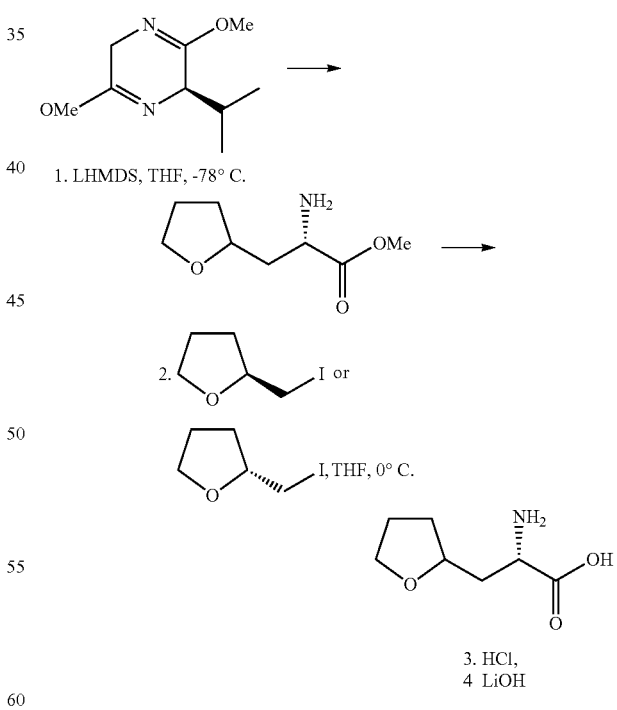

LHMDS (1.63 mL, 1.63 mmol) was added to a −78° C. solution of dihydropyrazine (300 mg, 1.63 mmol) in THF (10 mL). The mixture was kept at −78° C. for 30 minutes, followed by dropwise addition of a solution of 2-(iodomethyl)tetrahydrofuran (346 mg, 1.63 mmol; R or S-isomer in THF (5 mL). The mixture was gradually warmed up to 0° C. and stirred at this temperature overnight, followed by addition of aqueous HCl (1M, 5 mL). The mixture was kept at room temperature for 2 h and concentrated under reduced pressure. The residual material was purified by reverse-phase chromatography (HPLC, C18 column, water:methanol (0.05% TFA), 100:0 to 0:100), giving the corresponding methyl ester.

Lithium hydroxide (250 mg) was added to a solution of the methyl ester of Compound 7 or 8 (360 mg) in water (10 mL) and THF (10 mL) and stirred for 2 hours at room temperature. The solution was then adjusted to pH 6 with 1N hydrochloric acid and concentrated to dryness. The crude mixture was purified by reverse-phase chromatography (gradient of water: methanol (0.01% TFA), 100:0 to 90:10 over 30 minutes) to give the desired Compound 7 or 8 respectively.
Method 3: Alternate Method for Diastereoselective Synthesis of Both Diastereoisomers

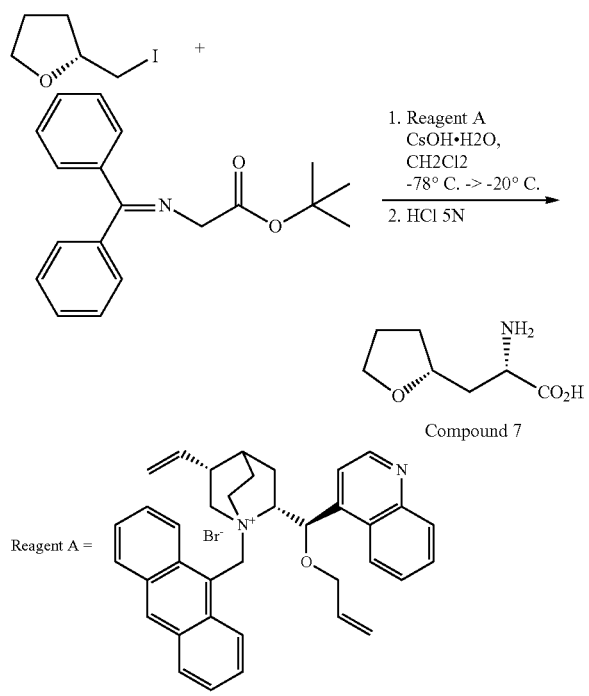

1—To a stirred −78° C. suspension of finely ground cesium hydroxide hydrate (10 g) were added N-(diphenylmethylene) glycine t-butyl ester (3.5 g), Reagent A (O-allyl-N-(9-anthracenylmethyl) cinchonidinium bromide, 712 mg), and R-2-(iodomethyl)tetrahydrofuran (3.73 g) in dichloromethane (10 mL). The mixture was allowed to slowly warm up to −20° C. and stirred at constant temperature overnight. The reaction mixture was worked up using ethyl acetate and water. The crude product was purified by silica gel chromatography (hexanes:ethyl acetate, 95:5 to 80:20 to afford 2.1 g of the diprotected amino acid.
2—A solution of the diprotected amino acid (2.1 g) from 1 in tetrahydrofuran (50 mL) and aqueous hydrochloric acid (5N, 25 mL) was heated under reflux for 3 hours. The resulting reaction solution was concentrated in vacuo. The residual material was dissolved in water and the solution was freeze dried. The solid was dissolved in water (containing 0.01% TFA) and purified by preparative HPLC (Gemini, water (0.01% TFA): acetonitrile, linear gradient 100:0 to 90:10 over 20 minutes) to afford Compound 7 (555 mg). $^1$H NMR (D$_2$O, 500 MHz) 1.59-1.65 (m, 1H), 1.87-1.98 (m, 2H), 2.09-2.14 (m, 2H), 2.15-2.21 (m, 1H), 3.78 (q, J=8.0 Hz, 1H), 3.88 (q, J=7.5 Hz, 1H), 4.08 (m, 1H), 4.16 (dd, J=6.0, 4.0 Hz, 1H).
Compound 8 was synthesized from S-2-(iodomethyl)tetrahydrofuran following the same procedure as described for Compound 7: $^1$H NMR (D$_2$O, 500 MHz) 1.58-1.65 (m, 1H), 1.87-2.00 (m, 3H), 2.12 (m, 1H), 2.23 (dt, J=15.5. 8.0, 4.5 Hz, 1H), 3.79 (q, J=7.5 Hz, 1H), 3.85 (q, J=7.5 Hz, 1H), 4.11 (dd, J=8.0, 5.0 Hz, 1H), 4.18 (m, 1H).

Example 2

In Vitro Affinity, $^1$H-gabapentin Binding Site a) Method 1:
Materials: Gabapentin is from TRC, [$^3$H]-Gabapentin is from GE Healthcare, and Meltilex A sheets (melt-on scintillator sheets) are from Perkin Elmer. Rat brain membranes are prepared in-house by conventional methods.

All solutions are prepared for the assay just before use, except for the membrane dilution. In each plate of vial a triplicate (3× each concentration for each compound tested), the following is added in this order: 1) 50 µl of diluted compound plate (500, 50 and 5 µM in water or DMS, 3 vials for each); 2) 50 µl of diluted Gabapentin/$^3$H-Gabapentin (200 nM in 0.5M Hepes/KOH (pH: 7.4), including 70 µCi of $^3$H-Gabapentin); and 3) 150 µl of rat brain membrane diluted to 500 µg/mL in 0.5M Hepes/KOH (pH: 7.4). The final compound concentration in the assay is 1, 10 and 100 µM. The same is done with a solution not containing the test articles as control. The test plate is then incubated for 30 minutes at room temperature with agitation. The binding reaction is terminated using a Tomtec cell harvester machine (Mach III M-FP-1). A meltilex sheet is placed on the filtermat (harvest from the assay) and is allowed to melt in the oven at 65° C. for 1 to 4 min. The filter is inserted in the plastic pouch, which is sealed and allowed to cool for 1 h before counting with a Microbeta Trilux counter (Perkin Elmer).

Results are calculated using the count per minutes (CPM) obtained for each sample with the Trilux. The CPM obtained for the control diluent represents the 100% binding of $^3$H-Gabapentin to membrane. The CPM obtained for the control gabapentin 100 µM represents the 0% binding. The % of binding for each compound is calculated by the formula:

$$\% \text{ of binding} = \frac{CPM \text{ of tested compound} - CPM \text{ of gabapentin}}{CPM \text{ of diluent} - CPM \text{ of gabapentin}} \times 100$$

A compound is considered positive if its % of binding is lower then 50%. Results in Table 2 are shown in % inhibition, as well as by their IC50 (concentration for 50% inhibition) and Ki (inhibitory constant) values, which are both calculated by standard methods from the results obtained.

TABLE 2

| Binding affinity to the Gabapentin binding site | | | | |
|---|---|---|---|---|
| | % inhibition | | | |
| ID | 1 µM | 10 µM | IC50 (µM) | Ki (µM) |
| Gabapentin | 80% | 90% | 0.07 | 0.05 |
| 4-HO-Ile* | 13% | 51% | 9.6 | 6.32 |
| Compound 6 | 82% | 92% | <1 | N/A |
| Compound 6A | N/A | N/A | 0.53 | 0.345 |

TABLE 2-continued

Binding affinity to the Gabapentin binding site

| | % inhibition | | | |
|---|---|---|---|---|
| ID | 1 μM | 10 μM | IC50 (μM) | Ki (μM) |
| Compound 6B | N/A | N/A | 0.32 | 0.207 |
| Compound 18 | 87% | 90% | 0.15 | 0.097 |

*(2S,3R,4S) 4-hydroxyisoleucine
N/A: not available b) Method 2:

Membrane preparation: cortices from 5 rats were homogenized in a 0.32 M sucrose solution containing 10 mM HEPES/KOH. Suspensions were centrifuged for 10 minutes at 2500×g and the supernatants were centrifuged at 48000×g for 20 minutes. Pellets were washed twice in 10 mM HEPES containing 1.25 mM EDTA and 1.25 mM EGTA and centrifuged at 48000×g. The final pellets were re-suspended in 10 mM HEPES/KOH. Protein concentration was determined using a BCA kit from Pierce (Rockford, Ill.). The quality of the preparation was assessed in a binding assay to gabapentin.

Binding assay: in 96-well plates, the selected compounds were incubated in 10 mM HEPES/KOH pH 7.4 at concentrations of 10 and 1 μM for 30 minutes at room temperature in the presence of 20 nM [$^3$H]-gabapentin and rat brain membranes (300 μg/mL of proteins). Radioactivity was assessed after filtration with the Tomtec cell harvester using a glass fiber filter A. Counts were obtained using the Microbeat Trilux counter.

Binding results: Effect of the tested compounds on the binding of [$^3$H]-gabapentin was determined by calculating the specific binding of [$^3$H]-gabapentin in the presence of the compound divided by the specific binding of [$^3$H]-gabapentin alone:

$$\% \text{ of binding} = \frac{([\text{total binding}]_s - [\text{non-specific binding}]_c)}{([\text{total binding}]_c - [\text{non-specific binding}]_c)} \times 100$$

wherein:
[total binding]$_s$ is the total binding of [$^3$H]-gabapentin in the presence of the compound;
[non-specific binding]$_c$ is the non specific binding of [$^3$H]-gabapentin in the presence of 100 μM cold gabapentin (c=control); and
[total binding]$_c$ is the total binding of [$^3$H]-gabapentin alone.

IC50 determination: IC50 was determined following incubation of crude rat brain membranes with varying concentrations of the tested compound (0.1 nM to 100 μM) in the presence of 20 nM [$^3$H]-gabapentin for 30 minutes at room temperature, as described in for the binding assay above. Table 3 shows % inhibition and IC50 results obtained using this method.

TABLE 3

Binding affinity to the Gabapentin binding site

| | % inhibition | | |
|---|---|---|---|
| ID | 1 μM | 10 μM | IC50 (μM) |
| Gabapentin | N/A | N/A | 0.25 |
| (2S)-Compound* | 61% (±8) | 16% (±3) | N/A |
| Compound 7 | 19% (±4) | 1% (±1) | 0.56 |
| Compound 8 | 11% (±1) | 0% (±2) | 0.48 |
| Compound 18 | 21% (±3) | 6% (±1) | N/A |

*(2S)-3-(2-furyl)alanine (see Example 1, method 1)
N/A: not available

Example 3

In Vivo Activity in Neuropathic Pain Rat Models

Neuropathic pain is a condition resulting from nerve injury or inflammation. The pain may persist for years even though the damaged tissues may have appeared to heal. Various experimental paradigms have been developed to mimic this human condition. The Chronic Constructive Model (CCI), Partial sciatic Nerve Ligation (PNL), Tibial Nerve Transection (TNT) and Spinal Nerve Ligation (SNL) models are recognized as stable and consistent models for neuropathic pain. To induce CCI, loose ligatures are tied around the proximal part of the sciatic nerve. PNL is induced by tight ligation of ½ of the sciatic nerve trunk. TNT is induced by ligation and transaction of the tibial nerve, one of the three major terminal branches of the sciatic nerve. To perform an SNL the L5 spinal nerve is ligated and transected. The procedures are undertaken on one side of the animal and the contra-lateral side serves as an internal control. Enhanced pain responses to thermal and/or mechanical stimulation are assessed by the Hargreaves' test and/or the von Frey fiber assay. In the Hargreaves' test, a radiant heat beam is projected on the plantar skin of each hind paw. The latency to paw withdrawal is recorded as a measure of the thermal pain threshold. Mechanical allodynia is determined by determining the 50% mechanical threshold with von Frey fibers using Dixon's up-and-down method. Using an SNL rat model (n=5) as described above and in Imamura Y et al (1995), *J. Pharmacol. Exp. Ther.*, 275(10), 177-82, results are obtained as in Table 4 below. Percentage inhibition of allodynia in rats with nerve ligation is calculated and upaired Stdent's t test is applied for comparison between vehicle control and treated group.

TABLE 4

Inhibition of neuropathic pain in rats

| ID | Dose (mg/kg) | % inhibition |
|---|---|---|
| Control (vehicle) | — | −5.0 ± 3.4 |
| Gabapentin | 200 | 61.0* ± 14.3 |
| Compound 18 | 200 | 55.7* ± 15.7 |

*Statistically significant from control values

Example 4

In Vivo Activity in a Metrazole-Induced Convulsions Model

A compound is tested in a model for convulsions (see Chen G et al. (1954), *Proc. Soc. Exp. Biol. Med.*, 87, 334. This model uses metrazole to induce convulsions. Prevention of ≥50% of metrazole (100 mg/kg)-induced clonic convulsions (2 points per mouse) and mortality (1 point per mouse) for a maximum score of 9. Results expressed in percentage (100%=9) for Compound 18 (200 mg/kg) as compared to gabapentin (100 mg/kg) or diazepam (1 mg/kg) are sown in Table 5.

TABLE 5

Prevention of convulsions in mice

| ID | Dose (mg/kg) | % Prevention |
|---|---|---|
| Control (vehicle) | — | 0 |
| Diazepam | 1 | 67 |
| Gabapentin | 100 | 67 |
| Compound 18 | 200 | 67 |

Example 5

In Vivo Activity in a Diabetes/Obesity Model

The objective of this study is to determine the effect of the compounds of the invention, namely Compounds 6A, 6B and 18, glycemia, insulin and body weight gain in a Diet-Induced Obesity (DIO) mouse model. Results are compared with (2S,3R,4S)-4-hydroisoleucine (positive control) and vehicle (negative control).

C57BL/6 mice are tested at 17-18 weeks of age and fed a high fat diet (60% of calories from fat) for 8 weeks. Fasted glycemia and body weight values are used to randomize the mice into control and treatment groups (n=8). The animals are treated twice dally (BID) (once on $7^{th}$ day) by oral gavage with 4-hydroxyisoleucine, Compounds 6A, 6B and 18 (100 mg per kg of body weight), and the control group receive vehicle (water) alone. The animals are treated for 7 days.

Oral glucose Tolerance Test (OGTT) is performed at 5 hours±30 minutes Post starvation (day 0 only) or Post AM test article administration (for day 7). Blood samples are collected via tail vein for glucose determination prior to glucose challenge (Pre-OGTT) and at 5, 10, 20, 30, 60, 90 and 120 minutes post-glucose administration. Glucose determination is perfomed using a hand held glucometer (Model OneTouch Ultra, LifeScan).

A second blood sample is also collected Pre-OGTT and at 5, 10, 60 and 120 minutes Post-OGTT for insulin determination. Insulin determination is done using an enzyme Immunoassay kit (Mecodia Ultrasensitive Mouse Insulin ELISA, ALPCO Diagnostics, Wndham, N.H.).

Body weight of the mice is measured at arrival, randomization, and on days 0, 3 and 7 of treatment. At the end of the study, the epididymal fat pads were isolated and weighed. Data are expressed as mean±SEM of body weight and mean±SEM of fat pad weight.

Figure 2:
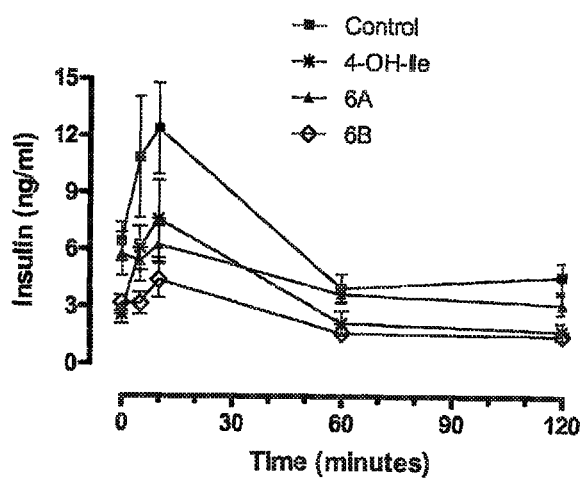
FIG. 2A shows insulin secretion during OGTT in DIO-mice treated with Compounds 6A and 6B, (2S,3R,4S)-4-hydroxyisoleucine (4-OH-Ile) and vehicle.
FIG. 2B shows insulin AUC following administration of Compounds 6A and 6B, 4-OH-Ile and vehicle in DIO-mice.
Figure 2:
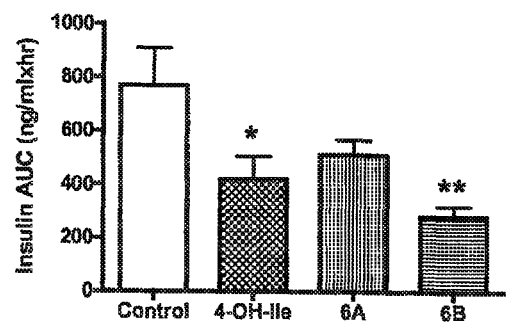

Results show that Compounds 6A and 6B exhibited neutral or beneficial effect on glycemia (FIG. 1A) and on Insulin (FIGS. 1B, 2A and 2B) when compared to control. Compound 18 showed no effect on glycemia.

The compounds tested did not show any significant effect on body weight as compared to vehicle treated mice. These results show that the compounds tested all have neutral or beneficial effect on metabolic parameters.

Example 6

Pharmacokinetic Profiles a) Pharmacokinetic Profiles in Mice

Compounds are tested for pharmacokinetic profile, including oral bioavailability in mice using the following procedure. Bioavailability estimates are performed after administration of 100 mg/kg of Compound 6B and 50 mg/kg of Compound 18 either Intravenously (IV) or orally (PO). Four animals per time point, per mode of administration are used. At each specific time point following drug administration, a blood sample is collected terminally (under isoflurane anesthesia) via cardiac puncture from each the 4 animals. Samples are collected at pre-dose and at 5, 15, 30, and 60 minutes and at 2, 4, 6, 8, 14 and 24 hours post oral administration and at pre-dose and 2, 5, 15, 30, and 60 minutes and 2, 4, 8, 14 and 24 hours post intravenous administration. Blood samples are collected into tubes containing $K_3$-EDTA as anticoagulant, kept on ice until centrifugation at 4° C. at a minimum speed of 3000 rpm (1620G) for 10 min. Plasma samples are harvested into polypropylene tubes, immediately placed on dry ice and stored at −80° C.

Figure 3:
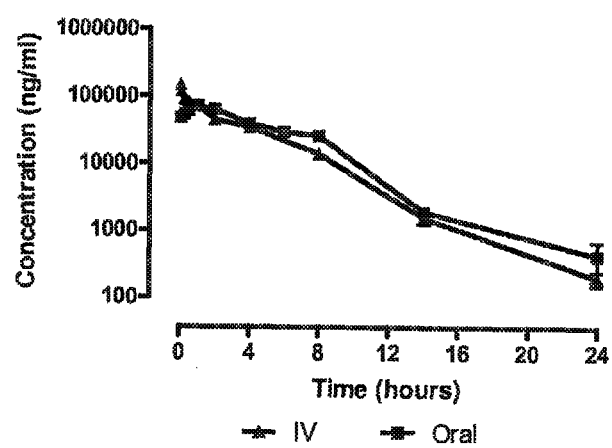
FIGS. 3A and 3B show pharmacokinetic profile (log scale) in mice following administration of Compound 6B (50 mg/kg) and Compound 18 (50 mg/kg) respectively i.v. and p.o.
Figure 3:
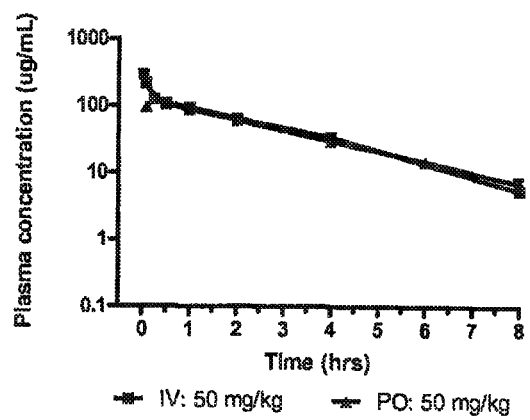

Compounds in mouse plasma are extracted using protein precipitation. Quantitation of the compounds in mouse plasma matrix is achieved using LC-MS detection. Sample concentration is calculated using a calibration curve. FIGS. 3A and 3B show mouse PK curves in log scale for Compounds 6B and 18 respectively. Bioavailability (% F) was about 100% for Compound 6B, and 88.4% for Compound 18.

b) Pharmacokinetic Profile in Dogs

Figure 4:
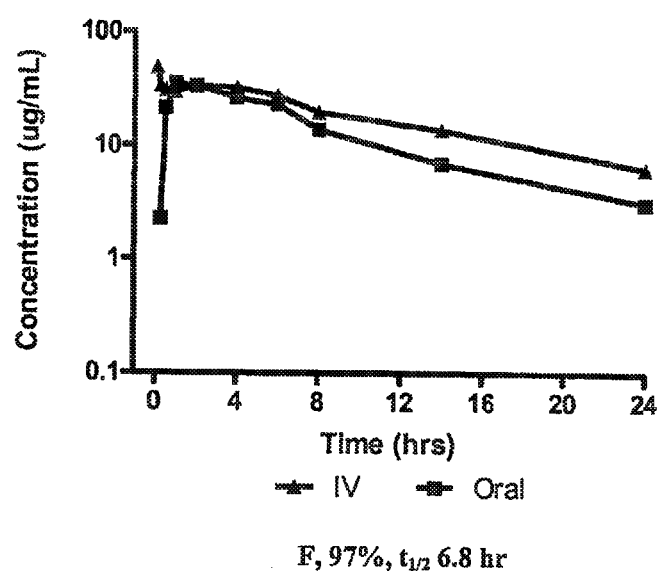
FIG. 4 pharmacokinetic profile (log scale) in dogs following administration of Compound 18 (25 mg/kg) p.o. and i.v.

The pharmacokinetic profile of Compound 18 is evaluated in one female Beagle dog. One single oral and one single IV dose of 25 mg/kg separated by a wash-out period are administered to the dog to get key preliminary information about the pharmacokinetics and oral bioavailability of Compound 18. The results are presented in FIG. 4. Compound 18 showed a classical first order type of pharmacokinetic profile at the dose administered with a terminal half live of around 7 hours. The compound is rapidly and very well absorbed following oral administration and does not demonstrate any significant first pass effect (oral bioavailability of 97%).

It is understood that the examples and embodiments described herein are for illustrative purposes only and that various modifications or changes in light thereof will be suggested to persons skilled in the art and are to be included within the spirit and purview of this application and scope of the appended claims.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A method for treating neuropathic pain in a subject in need thereof, comprising administering a compound or a pharmaceutically acceptable salt or ester thereof to the subject, the compound being selected from a compound of Formula IV:

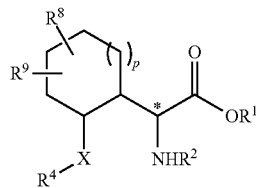

Formula IV wherein,

X is O, NH, or S;

$R^1$ is hydrogen, $C_{1-6}$alkyl, $C_{2-6}$alkenyl, $C_{2-6}$alkynyl, $C_{3-6}$cycloalkyl, $C_{3-6}$heterocycloalkyl, $C_6$aryl, or $C_{5-9}$heteroaryl;

$R^2$ is hydrogen, or an N-protecting group;

$R^8$ and $R^9$ are each independently hydrogen, $C_{1-12}$alkyl, $C_{6-10}$aryl, $NH_2$, $NHR^6$, $NR^6R^7$, $OR^6$, halide, cycloalkyl, alkylenyl, arylalkyl, or $R^8$ and $R^9$ are taken together with their adjacent atoms to form a spiro or fused heterocycloalkyl or heteroaryl group, or $R^8$ and $R^9$ are attached to the same carbon atom and together with the adjacent carbon atom form a carbonyl;

$R^4$, $R^6$ and $R^7$ are each independently hydrogen, $C_{1-12}$alkyl, or $C_{6-10}$aryl; and p is an integer from 1 to 2;

wherein when $R^1$, $R^2$, $R^4$, $R^6$, $R^7$, $R^8$ or $R^9$ is a group selected from alkyl, alkenyl, alkynyl, cycloalkyl, heterocycloalkyl, aryl, or heteroaryl, then said alkyl, alkenyl, alkynyl, cycloalkyl, heterocycloalkyl, aryl, or heteroaryl group may be unsubstituted or substituted with a group selected from the group consisting of acyl, unsubstituted amino, alkylamino, dialkylamino, arylamino, diarylamino, alkylarylamino, acylamino, carbamoyl, ureido, alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, and formyl;

such that neuropathic pain is treated in the subject;

wherein the neuropathic pain is associated with epilepsy.

2. A method for treating neuropathic pain in a subject in need thereof, comprising administering a compound or a pharmaceutically acceptable salt or ester thereof to the subject, the compound being selected from a compound of Formula IV:

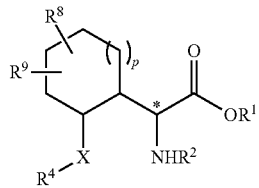

Formula IV wherein,

X is O, NH, or S;

$R^1$ is hydrogen, $C_{1-6}$alkyl, $C_{2-6}$alkenyl, $C_{2-6}$alkynyl, $C_{3-6}$cycloalkyl, $C_{3-6}$heterocycloalkyl, $C_6$aryl, or $C_{5-9}$heteroaryl;

$R^2$ is hydrogen, or an N-protecting group;

$R^8$ and $R^9$ are each independently hydrogen, $C_{1-12}$alkyl, $C_{6-10}$aryl, $NH_2$, $NHR^6$, $NR^6R^7$, $OR^6$, halide, cycloalkyl, alkylenyl, arylalkyl, or $R^8$ and $R^9$ are taken together with their adjacent atoms to form a spiro or fused heterocycloalkyl or heteroaryl group, or $R^8$ and $R^9$ are attached to the same carbon atom and together with the adjacent carbon atom form a carbonyl;

$R^4$, $R^6$ and $R^7$ are each independently hydrogen, $C_{1-12}$alkyl, or $C_{6-10}$aryl; and p is an integer from 1 to 2;

wherein when $R^1$, $R^2$, $R^4$, $R^6$, $R^7$, $R^8$ or $R^9$ is a group selected from alkyl, alkenyl, alkynyl, cycloalkyl, heterocycloalkyl, aryl, or heteroaryl, then said alkyl, alkenyl, alkynyl, cycloalkyl, heterocycloalkyl, aryl, or heteroaryl group may be unsubstituted or substituted with a group selected from the group consisting of acyl, unsubstituted amino, alkylamino, dialkylamino, arylamino, diarylamino, alkylarylamino, acylamino, carbamoyl, ureido, alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, and formyl;

such that neuropathic pain is treated in the subject;

wherein the neuropathic pain is associated with post-herpetic neuralgia.

3. The method of claim 1, wherein pain is controlled in the subject.

4. The method of claim 3, wherein said pain is nerve pain.

5. The method of claim 1, wherein X is an oxygen atom.

6. The method of claim 1, wherein X is NH.

7. The method of claim 1, wherein X is sulfur.

8. The method of claim 1, wherein p is 1.

9. The method of claim 1, wherein p is 2.

10. The method of claim 1, wherein $R^4$ is hydrogen.

11. The method of claim 1, wherein $R^2$ is hydrogen.

12. The method of claim 1, wherein $R^2$ is an N-protecting group selected from the group consisting of acyl, and amino-substituted acyl.

13. The method of claim 12, wherein said amino-substituted acyl is an amino acid residue linked through its carbonyl.

14. The method of claim 1, wherein said amino acid residue is selected from valyl, leucyl, and isoleucyl.

15. The method of claim 1, wherein the compound is of substantially pure S configuration.

16. The method of claim 1, wherein the compound is of substantially pure R configuration.

17. The method of claim 1, wherein the compound is a mixture of compounds where the chiral center C* is in the S or the R configuration.

18. The method of claim 1, wherein the compound is selected from the group consisting of:

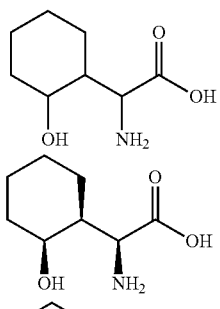
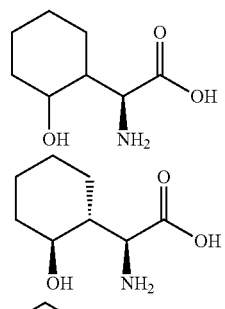
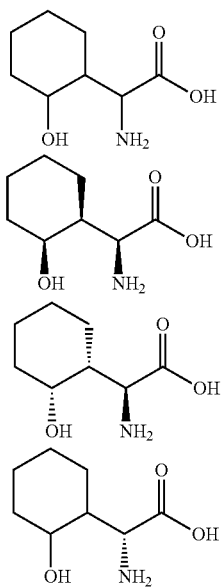
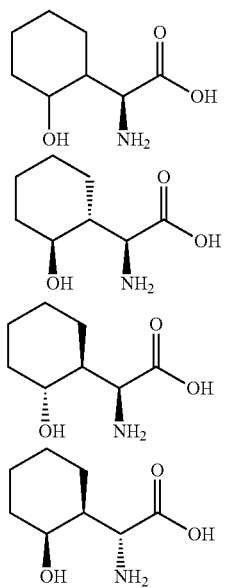
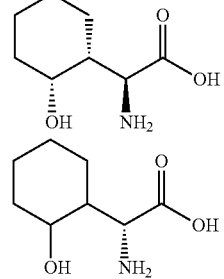
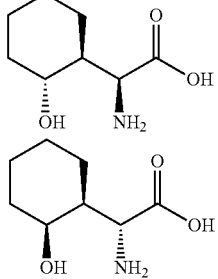

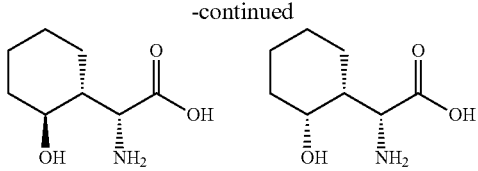

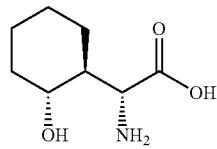

and pharmaceutically acceptable salts or esters thereof.

19. The method of claim 1, wherein the compound is

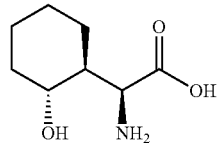

or a pharmaceutically acceptable salt or ester thereof.

* * * * *